US006541230B1

(12) United States Patent
Gordon et al.

(10) Patent No.: US 6,541,230 B1
(45) Date of Patent: Apr. 1, 2003

(54) DETOXIFICATION WITH SPONGES OR FOAMS CONTAINING PLURALITY OF ENZYMES AND ENCAPSULATED INDICATOR

(75) Inventors: Richard K. Gordon, Potomac, MD (US); Bhupendra P. Doctor, Potomac, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/559,396

(22) Filed: Apr. 26, 2000

Related U.S. Application Data
(60) Provisional application No. 60/130,988, filed on Apr. 26, 1999.

(51) Int. Cl.$^7$ .......................... C12N 11/18; C12N 11/02; C12N 11/08; C12N 9/96; C12S 13/00
(52) U.S. Cl. ...................... 435/175; 435/177; 435/180; 435/188; 435/262.5
(58) Field of Search ............................ 435/262.5, 177, 435/174, 178, 180, 182, 175, 188

(56) References Cited

U.S. PATENT DOCUMENTS

| | | | |
|---|---|---|---|
| 4,324,858 A | 4/1982 | Goodson et al. | 435/20 |
| 4,411,989 A | 10/1983 | Grow | 435/20 |
| 4,677,019 A | 6/1987 | Von Bluecher | 428/244 |
| 5,001,048 A | 3/1991 | Taylor et al. | 435/4 |
| 5,162,148 A | * 11/1992 | Boye et al. | 428/287 |
| 5,192,507 A | 3/1993 | Taylor et al. | 422/68.1 |
| 6,080,566 A | * 6/2000 | Cheng et al. | 435/196 |

FOREIGN PATENT DOCUMENTS

WO    WO 87 00914 A    2/1987

OTHER PUBLICATIONS

Braatz, (1994) "Biocompatible Pllyurethane–Based Hydrogel" in Journal of Biomaterials Applications, vol. 9.
Doctor, et al., (1991) "Enzymes as Pretreatment Drugs for Organophosphate Toxicity" Neuroscience & Biobehavioral Reviews, vol. 15, pp. 123–128.
Ember, (1997) "Detoxifying Nerve Agents" Chemical & Engineering News Sep. 15, 1997.
Gordon, et al., (1998) "Exploiting Immobilized Enzymes: Detoxification of Nerve Agents" Proceedings from the 6th CBW Protection Symposium, Stockholm, Sweden, May 1998.
Gordon et al., "Exploiting Immobilized Enzymes: Detoxification of Nerve Agents" in the Summary Digest of the 21st Army Science Conference, Jun. 15–17, 1998.
Gordon et al., (1997) "Potential Applications of Immobilized Cholinesterases: Tools for Protection, Decontamination, and Detection" in The ASA Newsletter 97–5, Issue No. 62.

Gordon et al., "Immobilized Enzymes–Selective and Specific Sensors for Organophosphate Chemical Toxins" a Proposal "White Paper" of Walter Reed Army Institute of Research. Jul. 1998, pp 2–10.
Gordon et al., (1990) "Vasoactive Intestinal Polypeptides Induce Guinea–Pig Ileum Contraction by Causing Release of Endogenous Acetylcholine" Arch. Int. Pharmacodvn. 305, pp 14–24.
Havens et al., (1993) "Reusable Immobilized Enzyme/Polyurethane Sponge for Removal and Detoxification of Localized Organophosphate Pesticide Spills" Ind. Eng. Chem. Research 1993, 32, 2254–2258.
LeJeune et al., "Fighting Nerve Agent Chemical Weapons with Enzyme Technology", Ann NY Acad. Sci. (1998) 864:153–170.
LeJeune et al., (1996) "Covalent Binding of a Nerve Agent Hydrolyzing Enzyme Within Polyurethane Foams" in Biotechnology and Bioengineering, vol. 51, pp. 450–457.
LeJeune et al., (1996) "Covalent Linkage of Mammalian Cholinesterases Within Polyurethane Foams" Proceedings from the 1996 Medical Defense Bioscience Review, pp. 223–230.
Medlin, (1998) "Super Sponges" Environmental Health Perspectives, vol. 106, No. 4, pp. A182–184.
Lejeune, et al., 1999 "Biocatalytic Nerve Agent Detoxification in Fire Fighting Foams" Chemical Abstracts, vol. 130, No. 19.
Russell, 1995 "Biocatalytic Nerve Agent Decontamination with Protein–Polymers" Univ. Pittsburgh Proposal to USAMRMC.
"Reactivation of Various OP Inhibited Immobilized (Sponge) FBS–AchE with HI–6" Table of data. Fax from Doctor, Dec. 21, 1995.

(List continued on next page.)

Primary Examiner—David M. Naff
(74) Attorney, Agent, or Firm—Elizabeth Arwine

(57) ABSTRACT

A reusable sponge or foam made of a polymer such as polyurethane is prepared containing a plurality of different enzymes or a cross-linked complex of the plurality of enzymes for detoxification of a diverse array of hazardous chemicals such as organophosphorus and/or organosulfur compounds. The plurality of enzymes include enzymes selected from acetylcholinesterase, butyrylcholinesterase, triesterase, pseudocholinesterase, choline oxidase, peroxidase, organophosphate hydrolase, phosphotriesterase, paraoxonase and laccase. A preferred mixture of enzymes contains organophosphate hydrolase and acetylcholinesterase or butyrylcholinesterase. The sponge or foam may additionally contain carbon, an enzyme reactivation compound and/or an indicator for measuring capacity for detoxification. The indicator can be fluorescent, chemiluminescent or visible chromogen or an electrode, and be encapsulated in a liposome or crushable packet. The sponge or foam may be color-coded to indicate specific chemical detoxified, or to indicate enzymatic concentration, activity and/or remaining shelf-life. A kit is formed containing the sponge or foam and the compound for enzyme reactivation.

11 Claims, 29 Drawing Sheets

OTHER PUBLICATIONS

"Abstract: Covalent Linkage of Mammalian Cholinesterases and OP Hydrolyzing Enzymes Within Polyurethane Foams" Fax from Doctor to Russell Feb. 27, 1996 and fax from Madeya to Russell, Feb. 28, 1996.

Russell, Jun. 4, 1996 "White Paper: Biotechnology Versus Chemical Weapons: A Battle for the 21st Century. The Use of Stabilized Enzymes to Decontaminate and Demilitarize".

LeJeune, et al., "Dramatically Stabilized Phosphostriesterase—Polymers for Nerve Agent Degradation" Biotechnol & Bioengin, vol. 54 No. 2, Apr. 20, 1997, pp 105–113.

"Abstract: Covalent Linkage of Mammalian Cholinesterases Within Polyurethane Foams" Fax from Doctor to Russell, Jun. 10, 1996. Submitted to the Proceedings of the 1996 Medical Defense Bioscience Review.

"Proceedings of the CB Medical Treatment Symposium: An Exploration of Present Capabilities and Future Requirements", Jul. 7–12, 1996, Spiez, Switzerland, pp 374–379.

"Data Tables regarding polyurethane foam sponges" Fax from Doctor to LeJeune Apr. 17, 1997.

Solicitation DAA 005–97–I–1981, Contractor Russell for Synthesis work. Includes Univ. Pittsburgh data tables regarding synthesis.

Slide, notes indicate that prepared Sep. 22, 1997 and presented Oct. 15, 1997, Univ. Pittsburgh Seminar.

Slide, notes indicate that prepared Sep. 15, 1997 and presented Sep. 19, 1997, W.V.U. Grad Student Symposium.

Slide, notes indicate that prepared Nov. 21, 1996 and presented 4/97, ACS Meeting.

LeJeune, 1997 "Biotechnology versus Chemical Weapons: Implementing Enzyme Technology in Bioremediation" Proposal to Department of Chemical Engineering, Carnegie Mellon Univ, pp 10, 12 & 13.

Russell, Nov. 13, 1997, "Biotechnology versus Chemical Weapons: Implementing Enzyme Technology in Decontamination/Demilitarization" Proposal to Edgewood Research, Development and Engineering Center, pp 1–33.

* cited by examiner

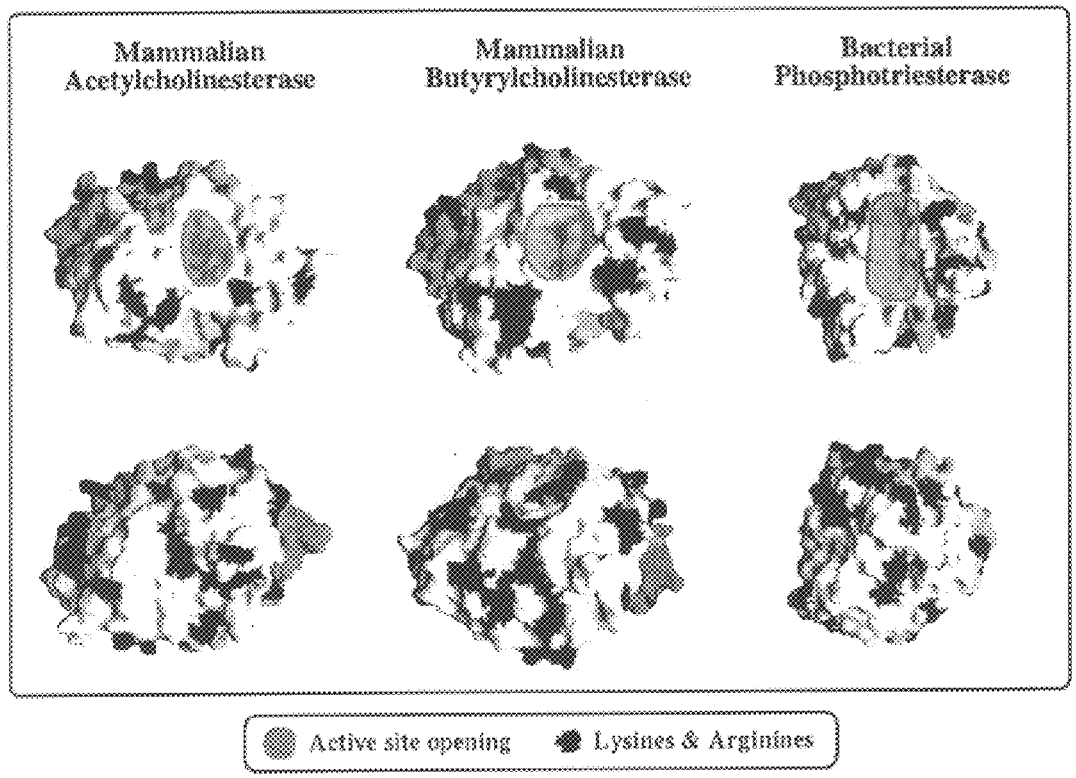

Figure 1A. Modeled surfaces of ChEs and triesterase. The top row shows a view of the front of the enzymes with the lip of the active site gorge outlined with a dotted line in the center. The bottom row shows the backside of the enzymes (180° rotation). The Lysine and Arginine residues on the surface, which are potential coupling sites to the polymer, are shaded dark in both the top and bottom row.

Similarly, a model of the surface of laccase is shown with available residues to couple covalently to the prepolymer (top, front of enzyme; bottom, backside of enzyme).

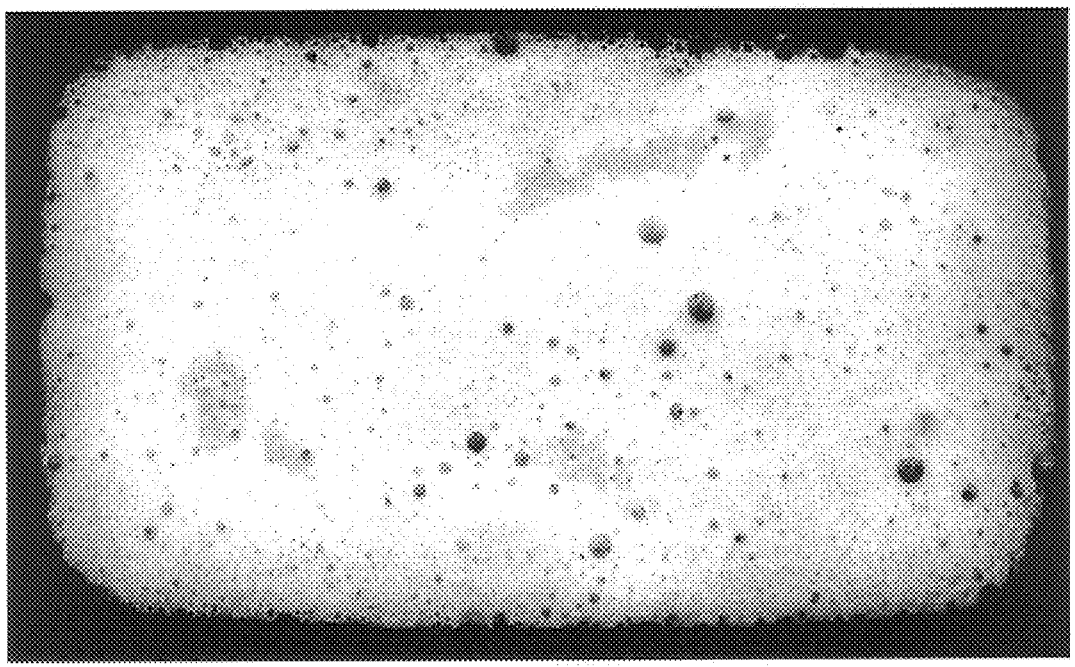
Figure 2. Final product: FBS-AChE sponge

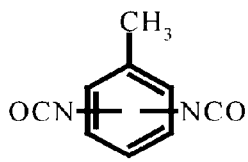
TDI prepolymer functional group
1. Aqueous Initiation of Polymerization
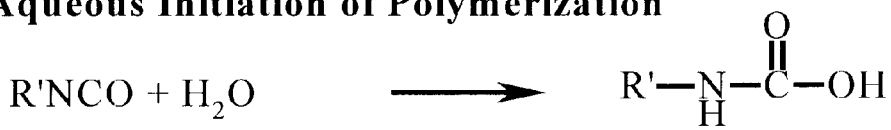
2. Amine Formation and CO₂ Evolution (foaming)
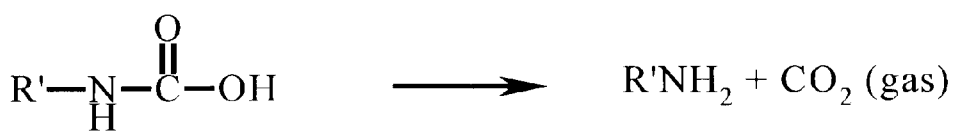
3. Prepolymer Crosslinking
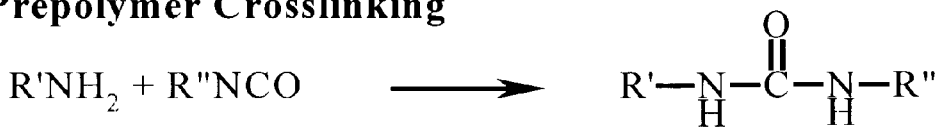
4. Covalent ChE Incorporation at Aliphatic Amino Group(s)
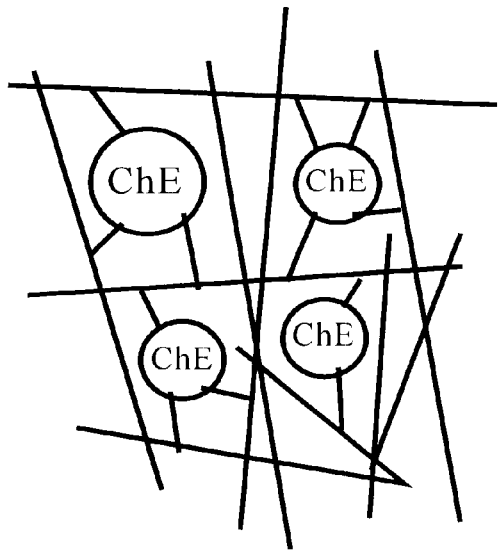
**polyur

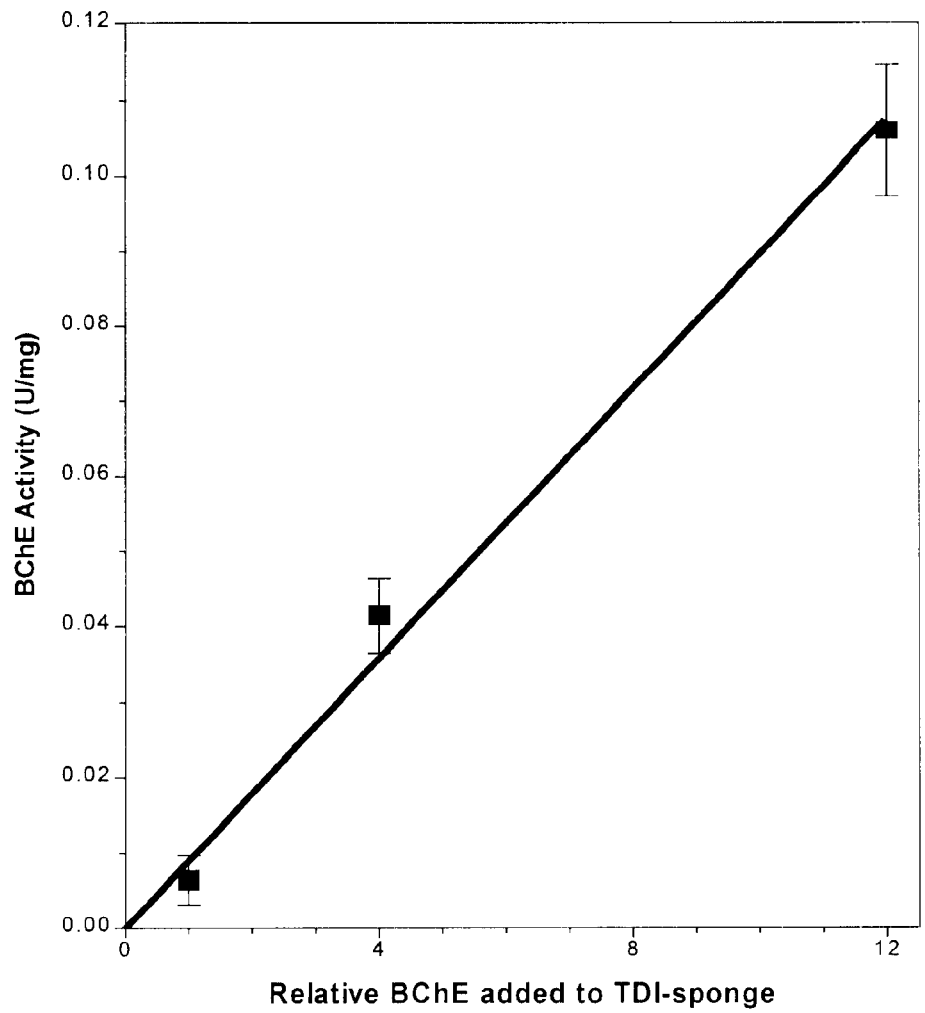
Figure 4. A linear correlation was observed between the amount of BChE added to the prepolymer during synthesis and the amount of BChE activity observed in the final sponge.

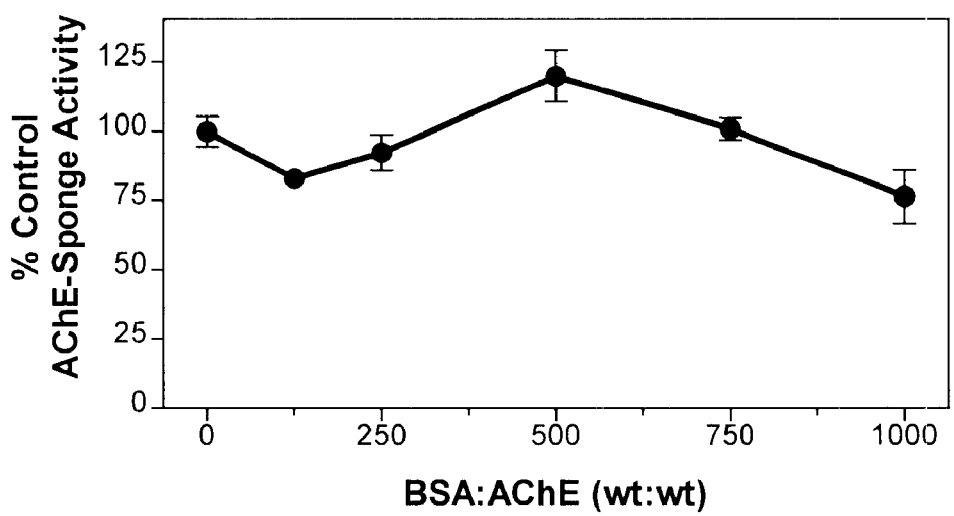
Figure 5. Increasing amounts of BSA were added during synthesis to a constant amount of AChE and TDI polymer

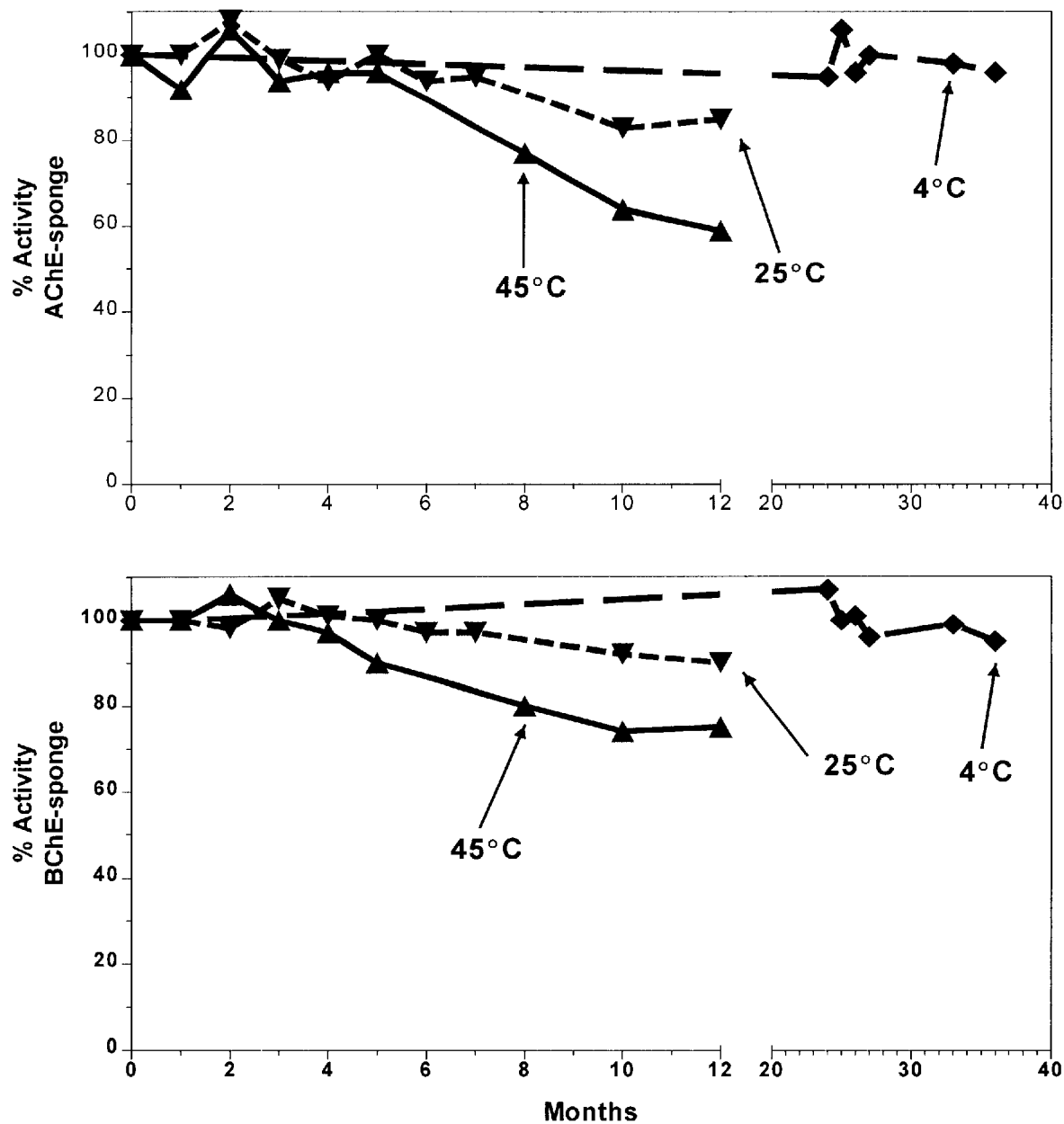
Figure 6. Stability of AChE (top) and BChE (bottom) sponges at various temperatures.

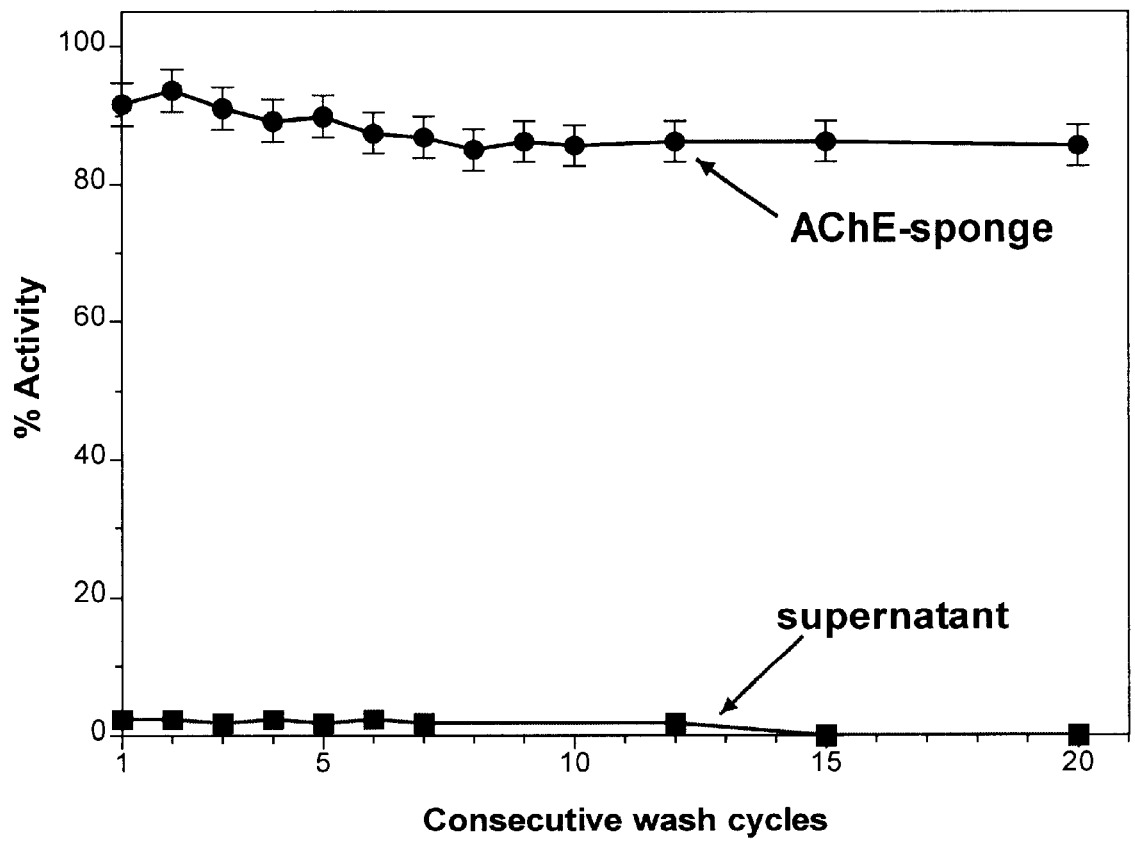
Figure 7. An AChE-sponge was alternately washed with phosphate buffer and assayed for activity. This procedure was carried out for three days. Similar results were observed for BChE-sponge.

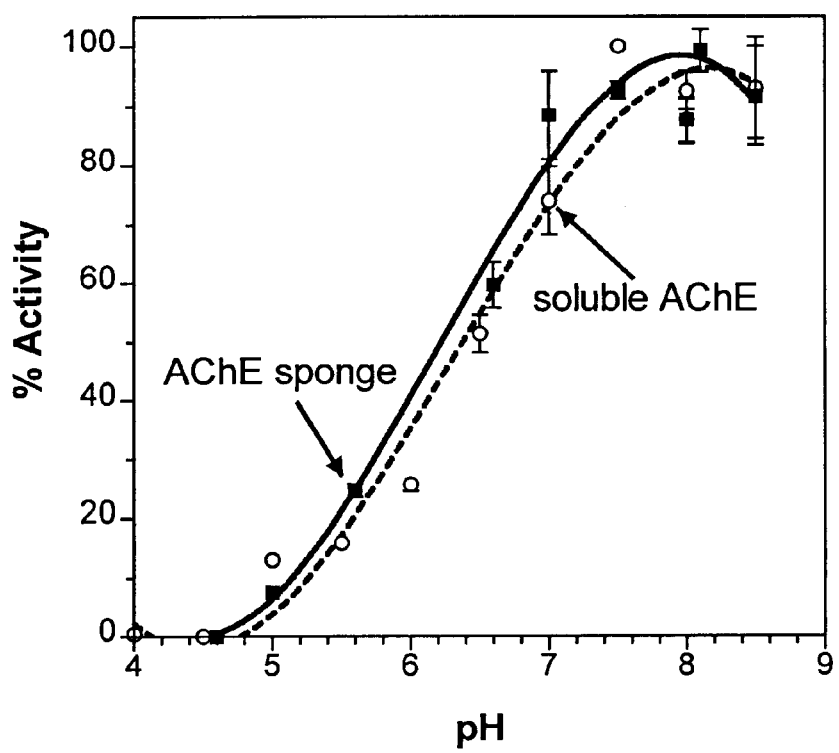
Figure 9. pH profile of soluble and immobilized acetylcholinesterase.

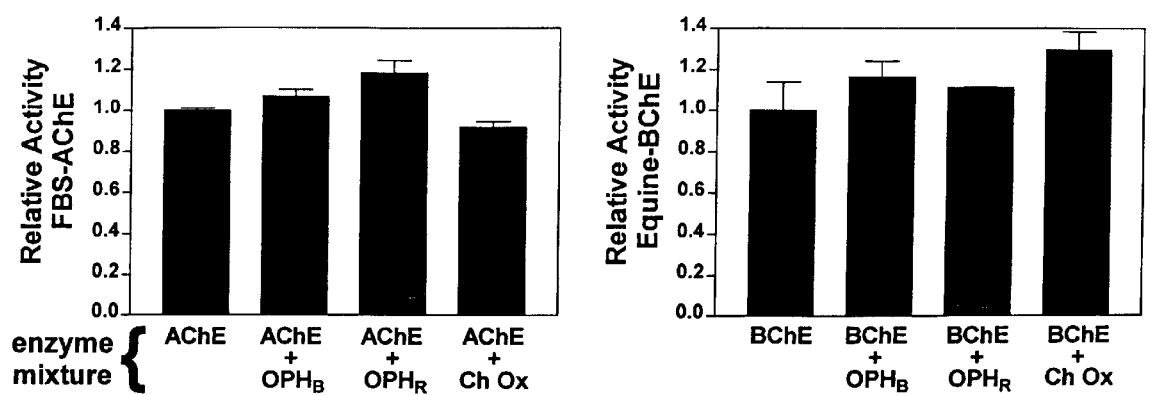
Figure 10. Co-immobilization of ChEs and OP hydrolases.

Figure 11A shows a version of a manual mixing gun and Figure 11B shows a disposable mixing stator. Complete mixing of the enzyme in aqueous solution and the viscous prepolymer is accomplished in the stator. The product shown here for illustrative purposes is green, while the two starting components are yellow and blue.

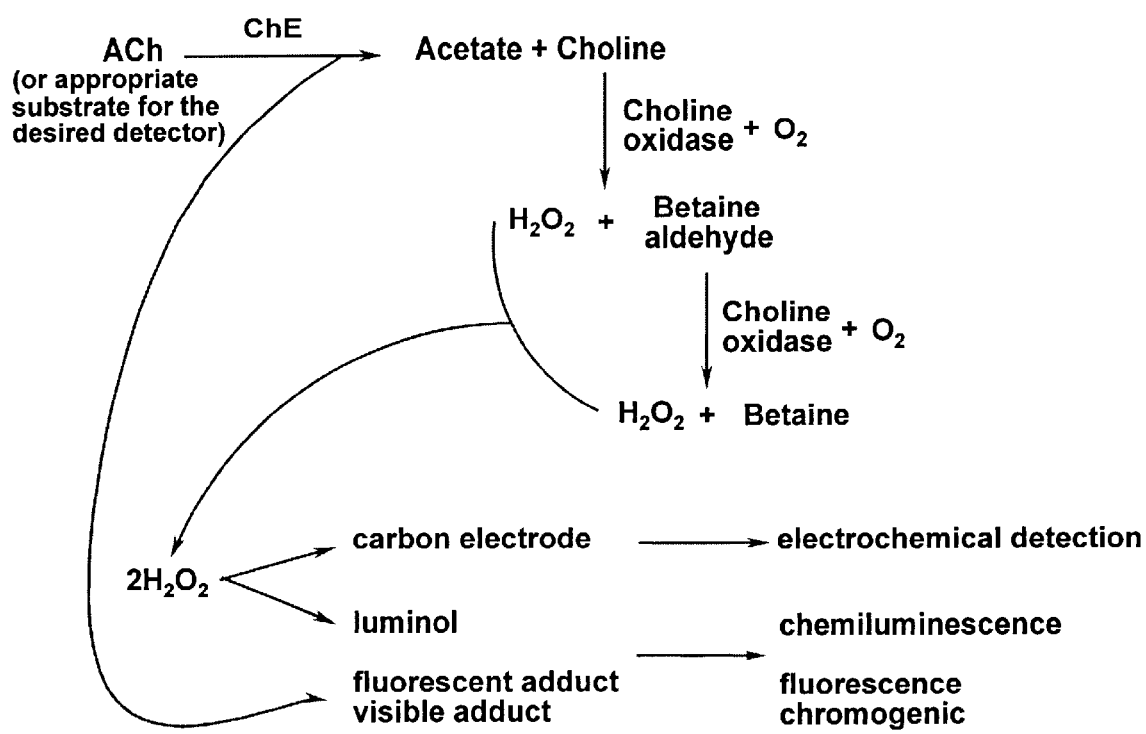
Figure 12. Alternate schemes for detecting cholinesterase activity in the biosensor. This figure shows a variety of possible detection methods, such as qualitative colorimetric changes, chemiluminescent for a dark environment, and additional amplification by coupling the ChE reaction to choline oxidase.

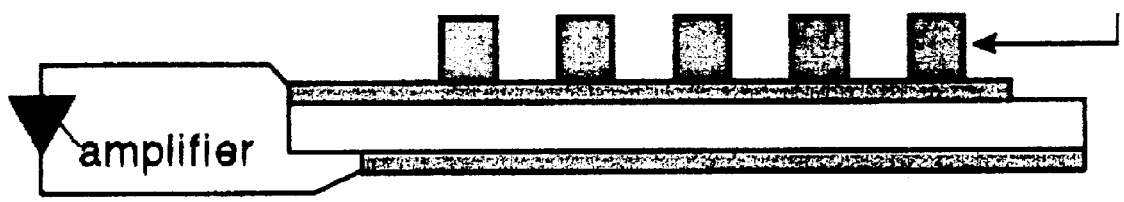
Figure 13. Model of a carbon electrode with immobilized cholinesterase enzyme.

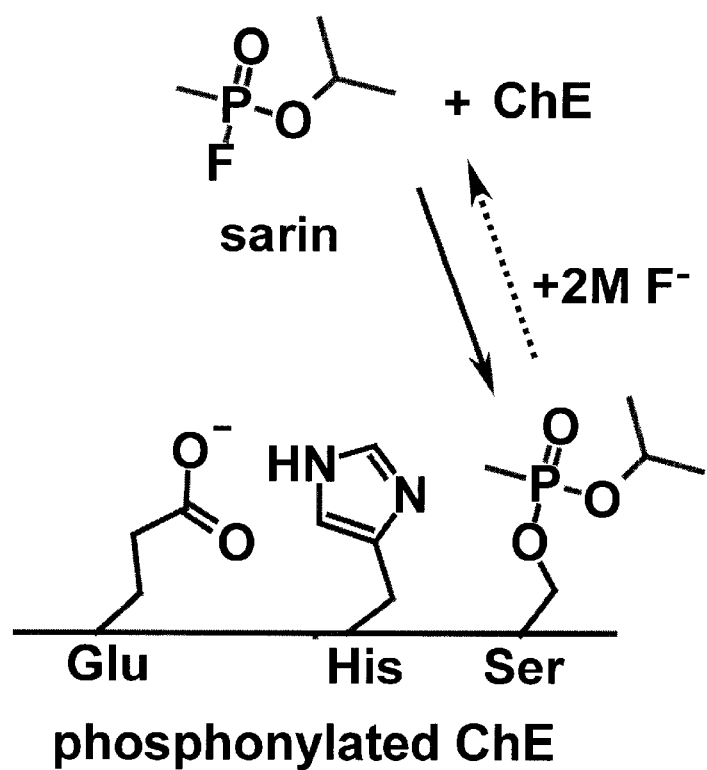
Figure 14. Using high fluoride ion concentrations to reverse the reaction between the OP and ChE. This reaction will permit the determination of the type of OP bound to the badge.

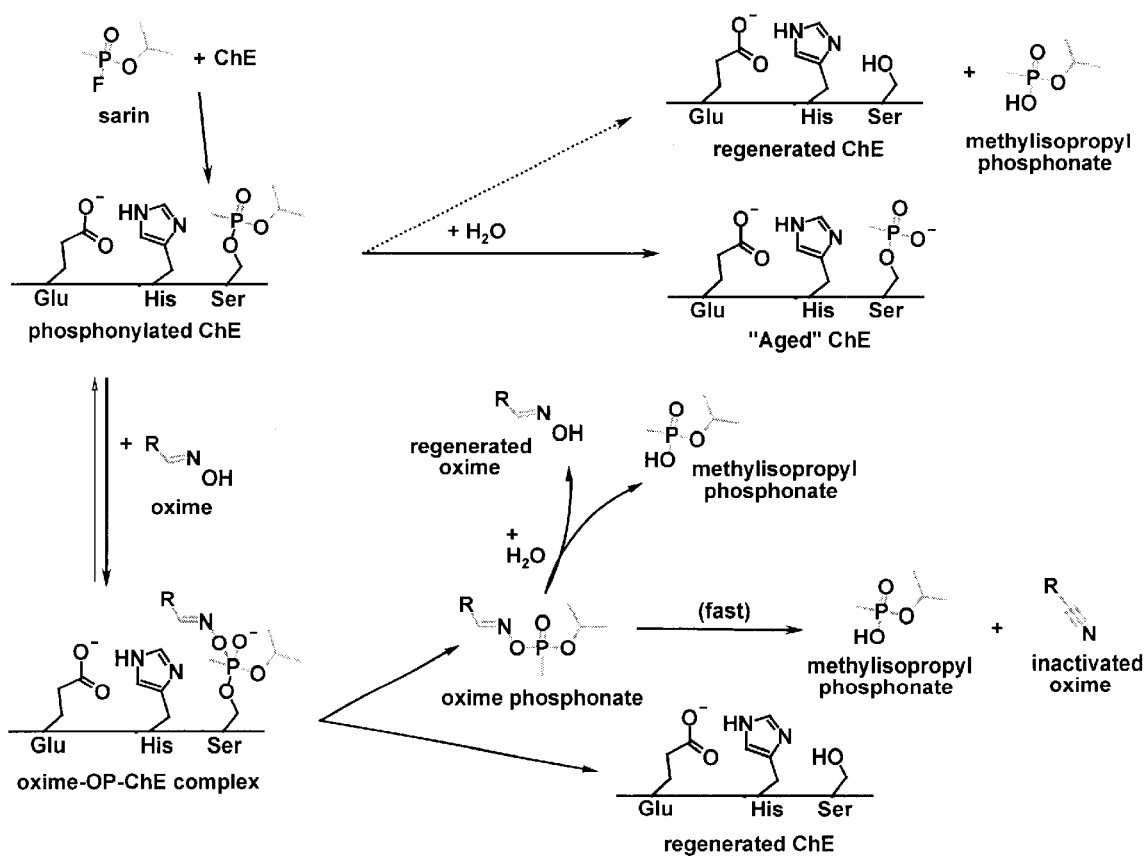
Figure 15 Reactivation of Alkylphosphorylated ChE with Oxime

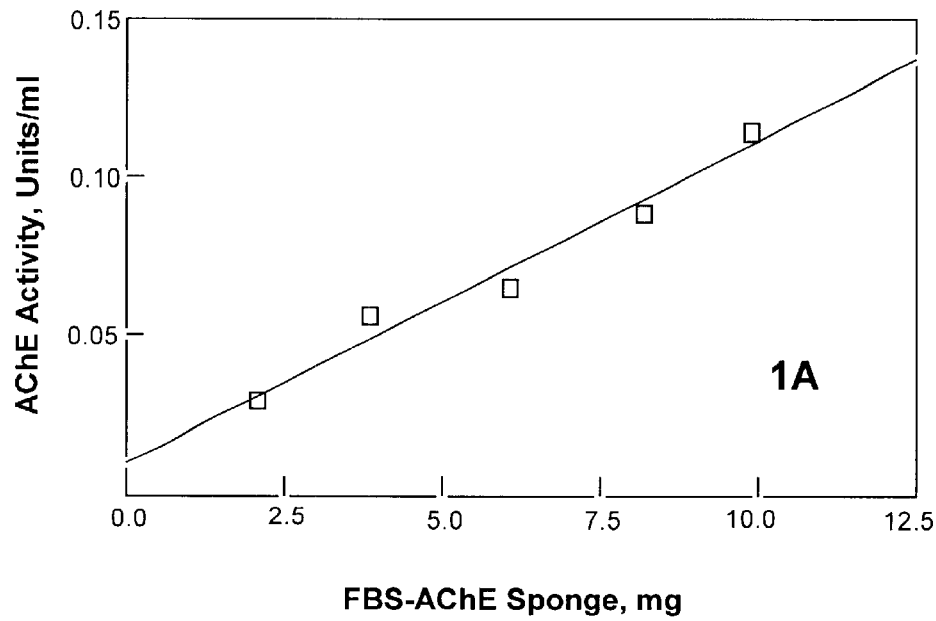
Figure 16A. Enzyme activity of immobilized FBS-AChE.
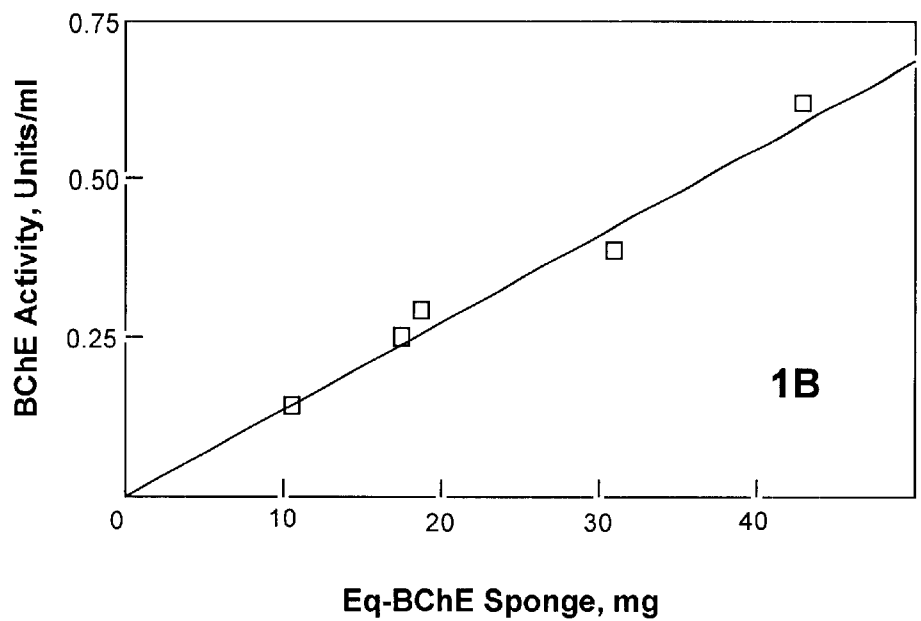
Figure 16B. Enzyme activity of immobilized Eq-BChE.

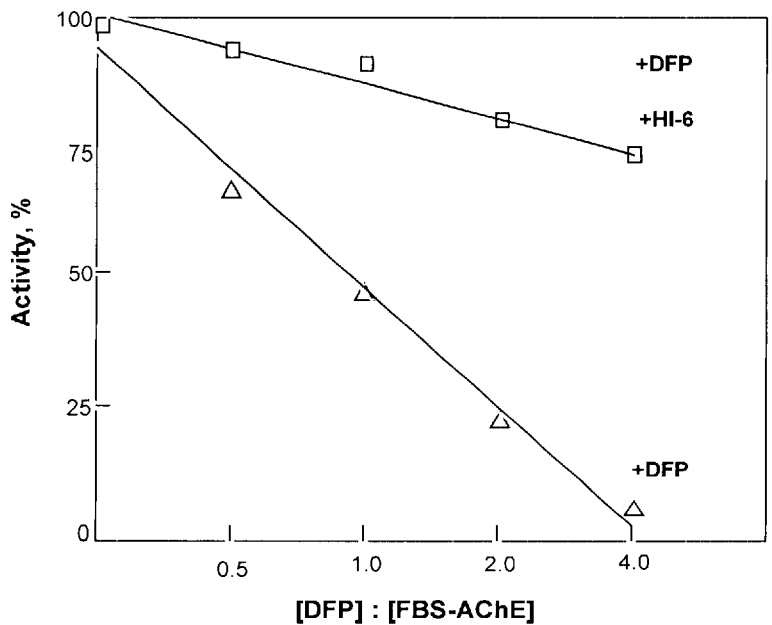
Figure 17. Inhibition of foam-immobilized FBS-AChE by DFP and reactivation by HI-6.
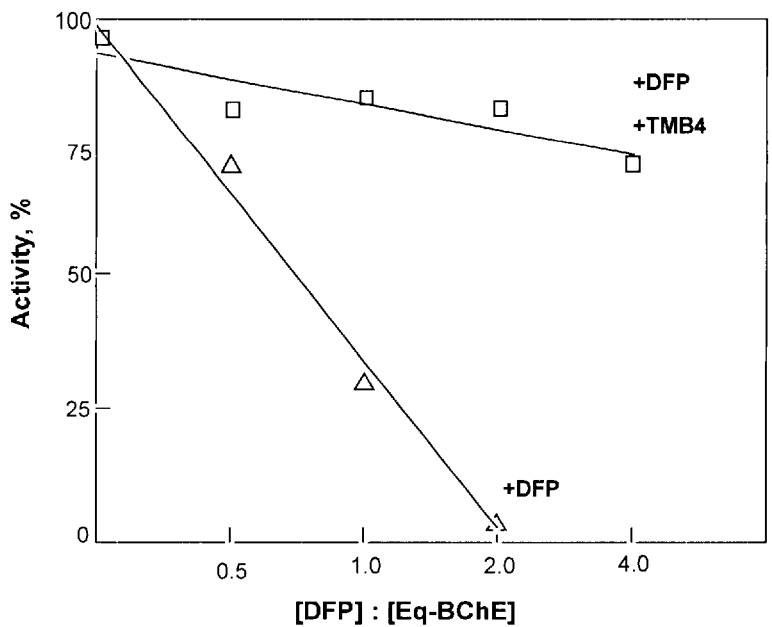
Figure 18. Inhibition of foam-immobilized Eq-BChE by DFP and reactivation by TMB4.

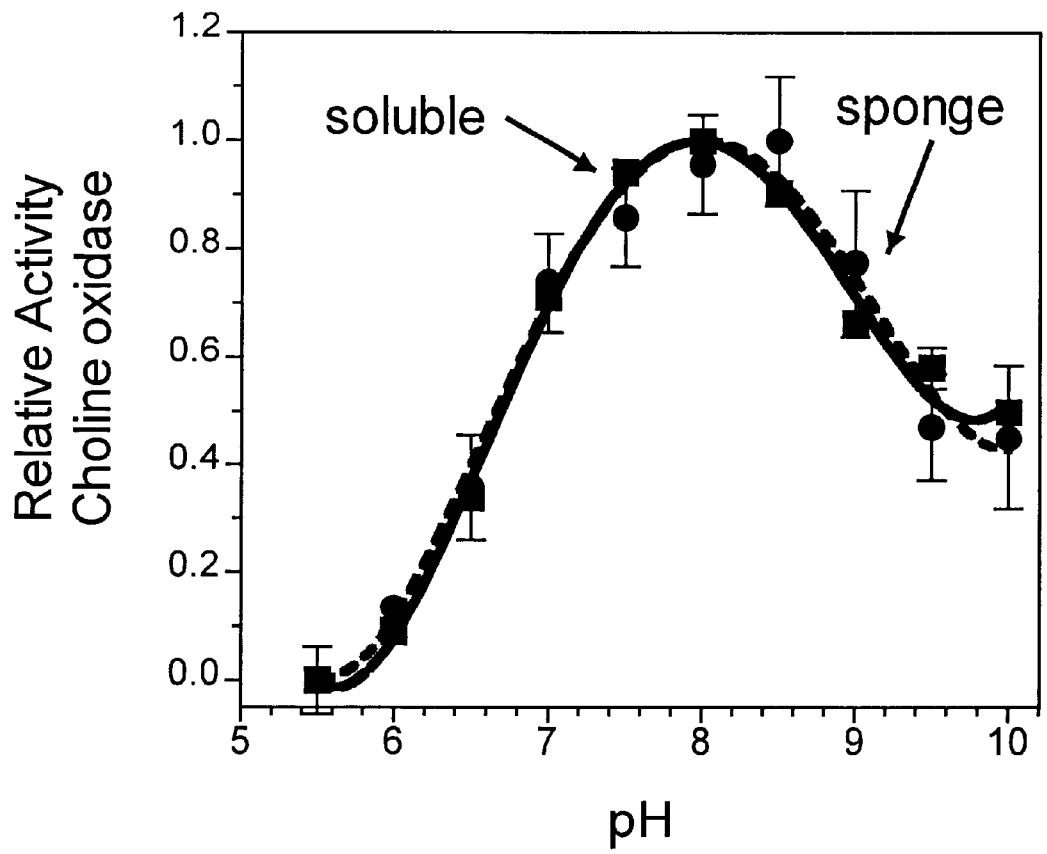
Figure 20A: The pH profile of soluble and immobilized choline oxidase.
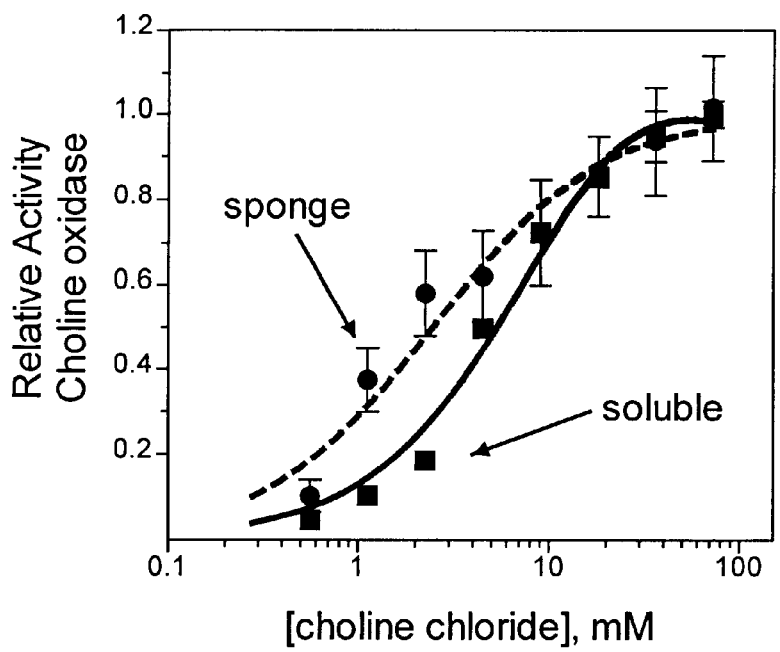
Figure 20B: Substrate concentration dependent curve for soluble and polyurethane coupled choline oxidase.

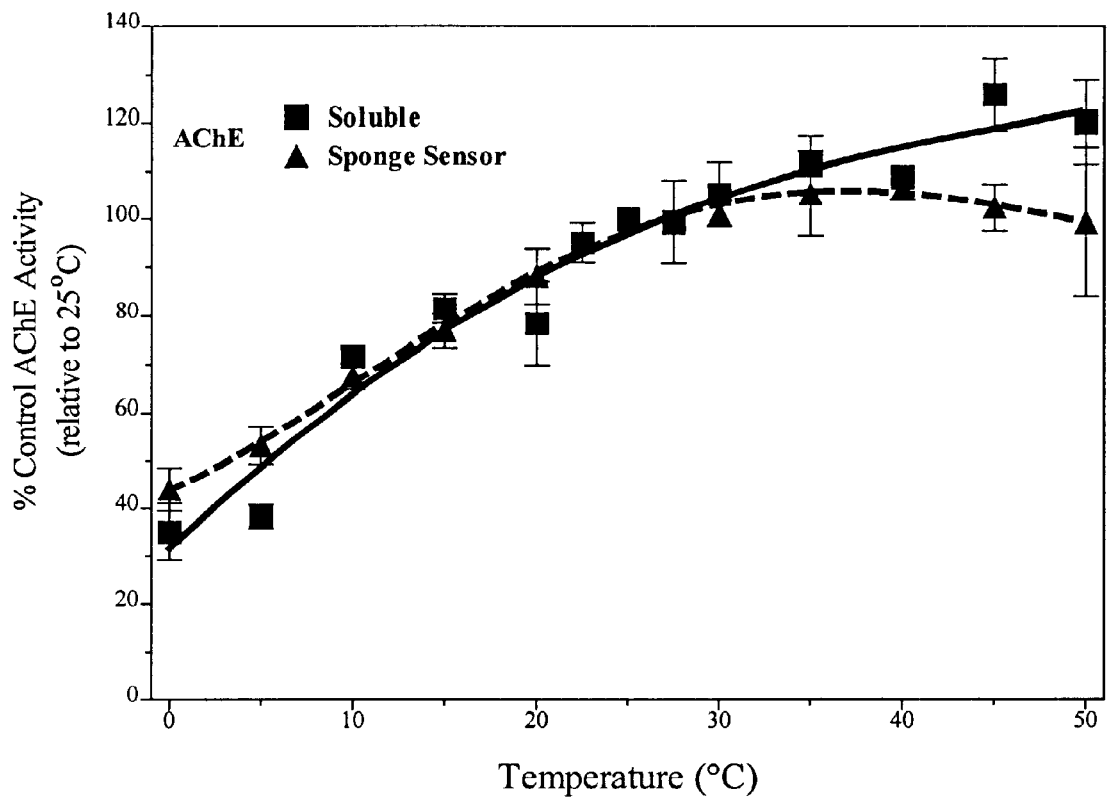
Figure 21A. Temperature profile of Immobilized and Soluble AChE
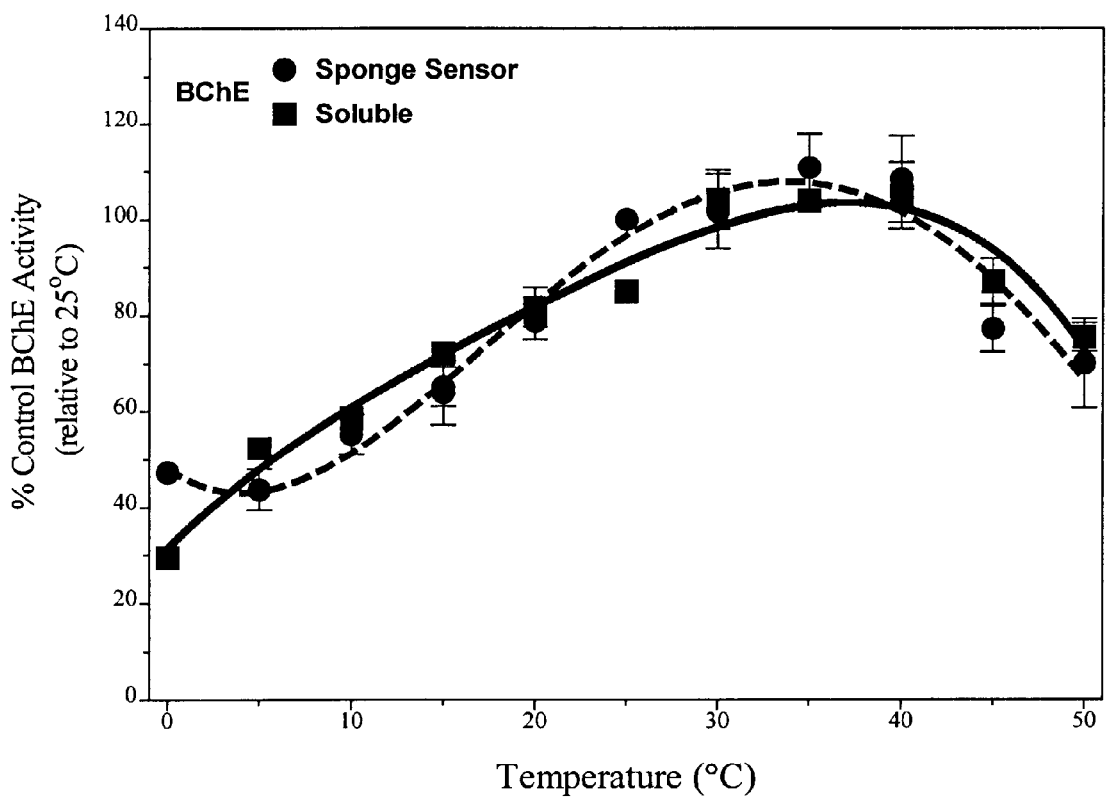
Figure 21B. Temperature profile of Immobilized and Soluble BChE

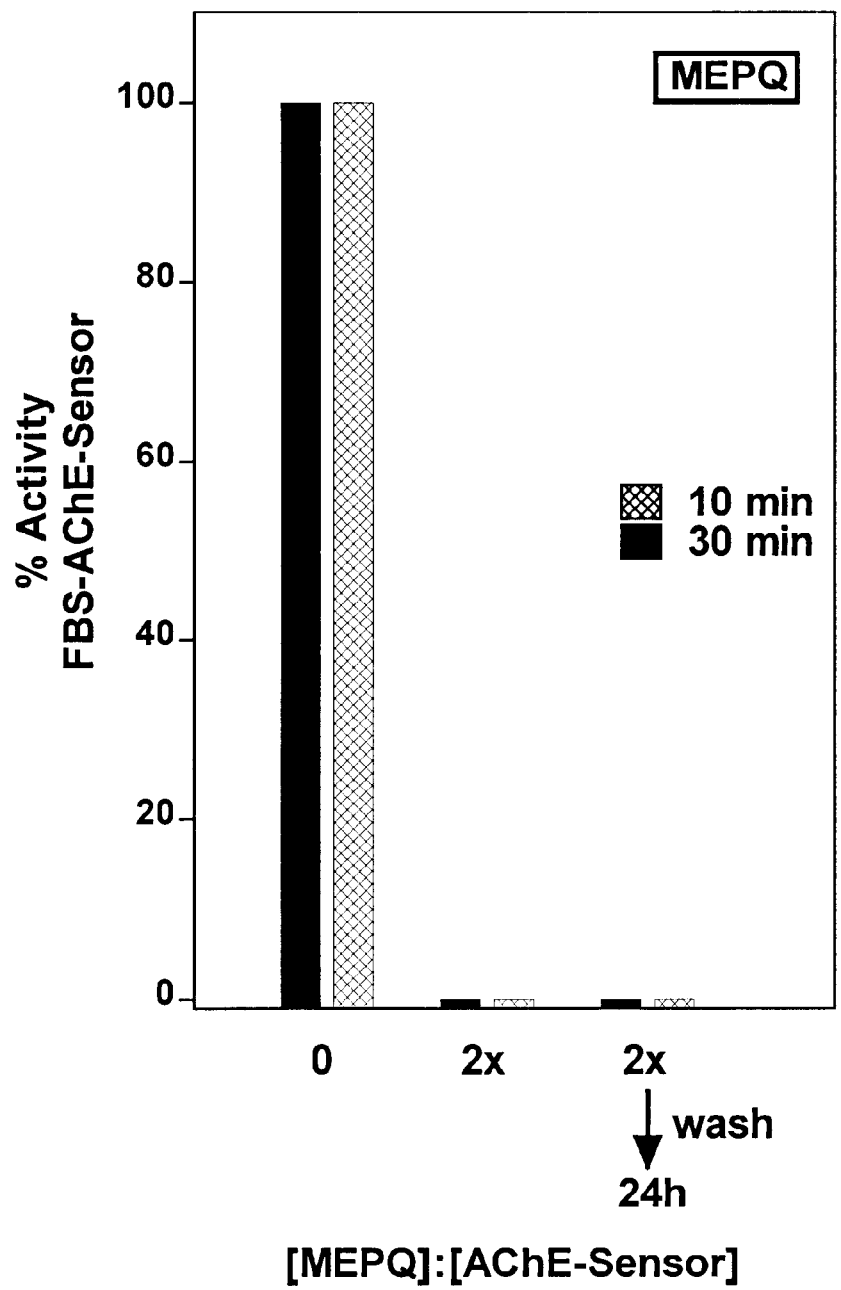
Figure 23: Inhibition of AChE-sensor by the organophosphate MEPQ, which is not reversed by washing in water or buffer.

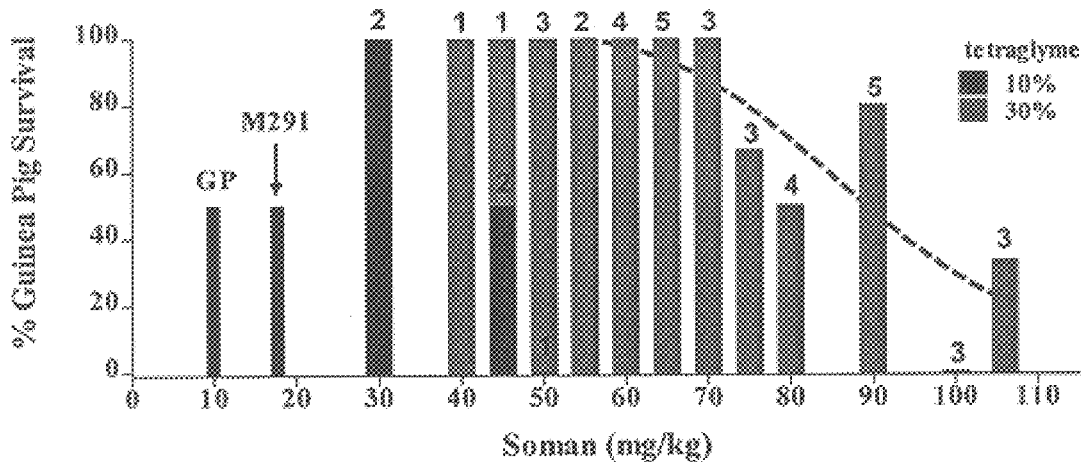
Figure 24A: protection afforded by sponge with tetraglyme additive.
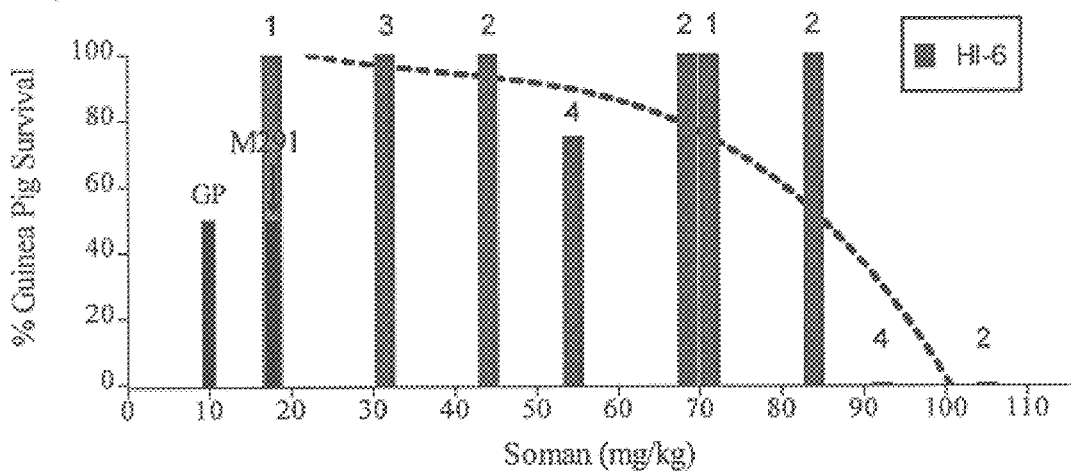
Figure 24B: protection afforded by sponge with HI-6 additive.
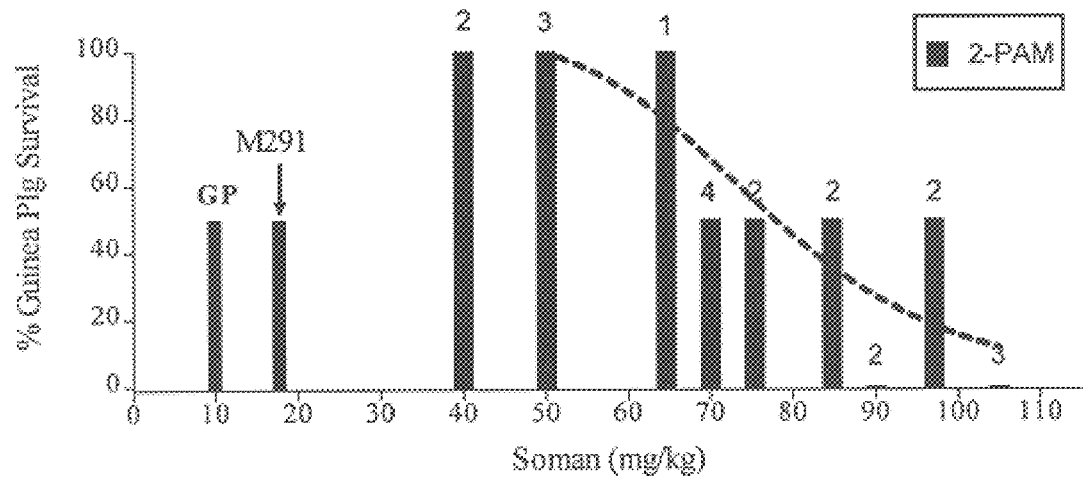
Figure 24C: protection afforded by sponge with 2-PAM additive.

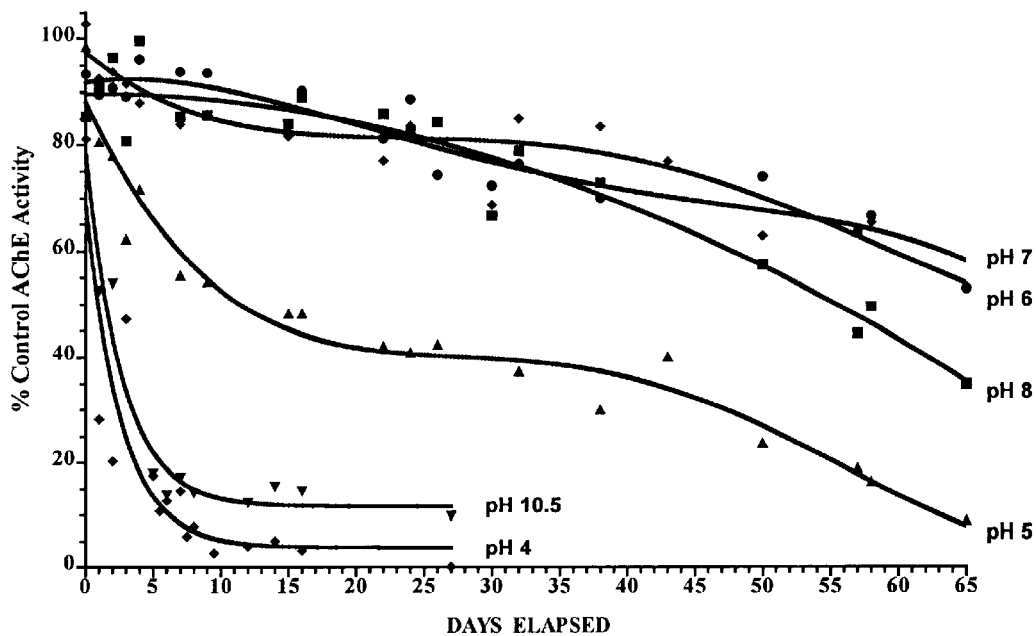
Figure 26A: AChE-Sensor Activities after Continuous Incubation at 25°C at Different pHs
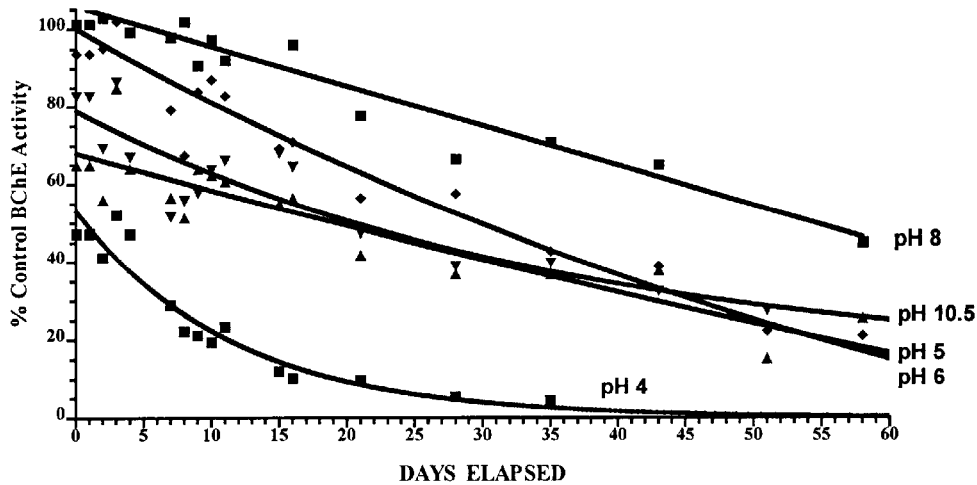
Figure 26B: BChE-Sensor Activities after Continuous Incubation at 25°C at Different pHs

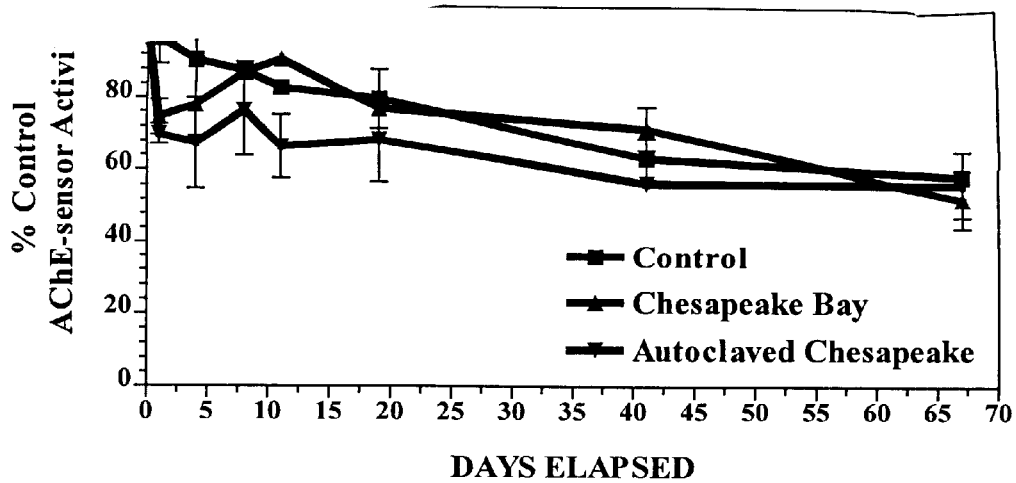
Figure 26C. AChE-Sensor Activity after Continuous Exposure to Chesapeake Bay (Brackish) Water at 25°C
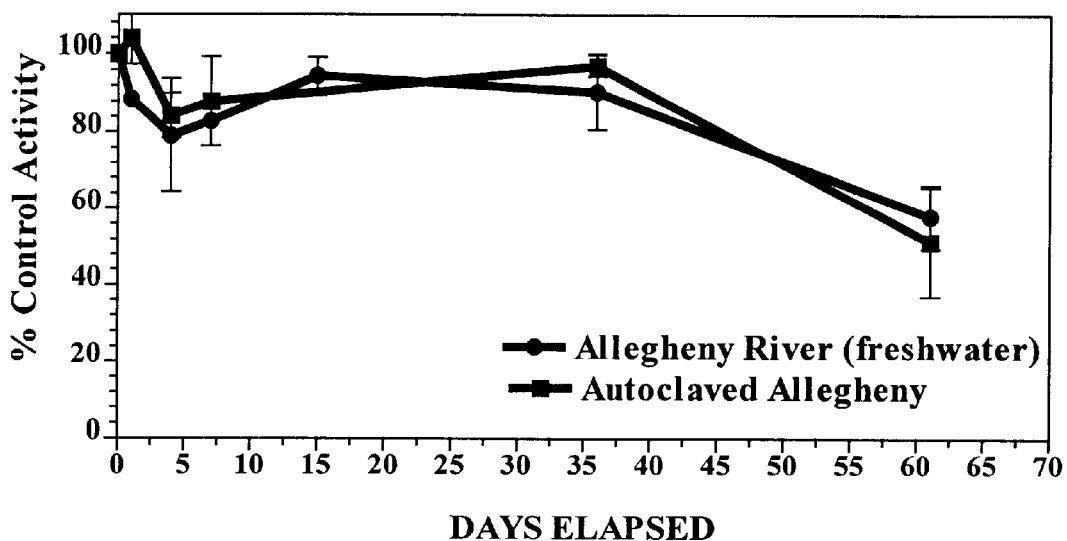
Figure 26D: AChE-Sensor Activity after Continuous Exposure to Allegheny River (Fresh) Water at 25°C

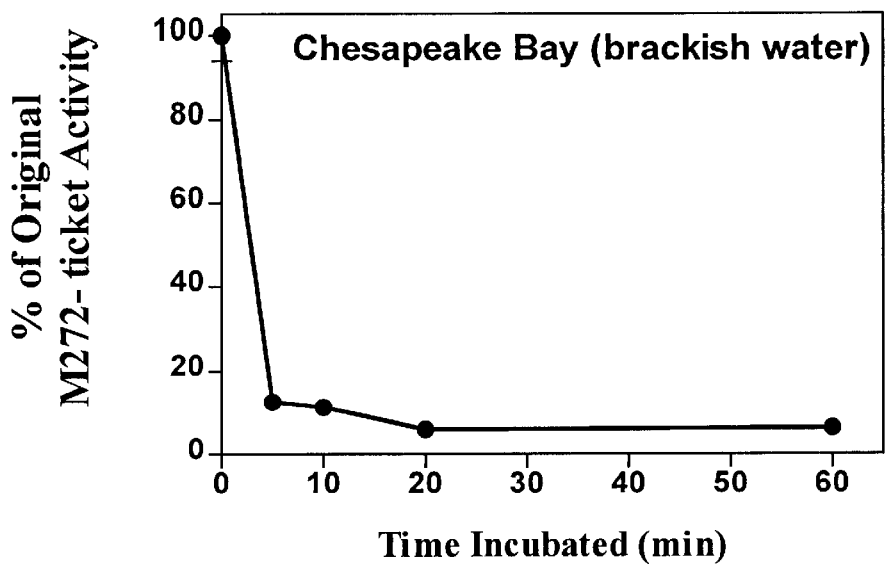
Figure 26E. Sensitivity of M272 ticket to aqueous conditions (Chesapeake Bay brackish water)
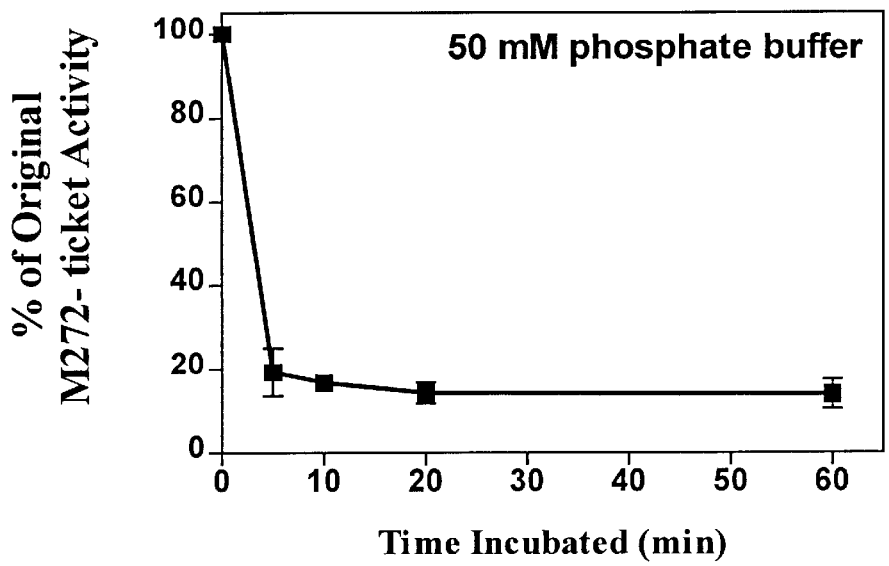
Figure 26F. Sensitivity of M272 ticket to aqueous conditions (50 mM phosphate buffer, pH 8.0)

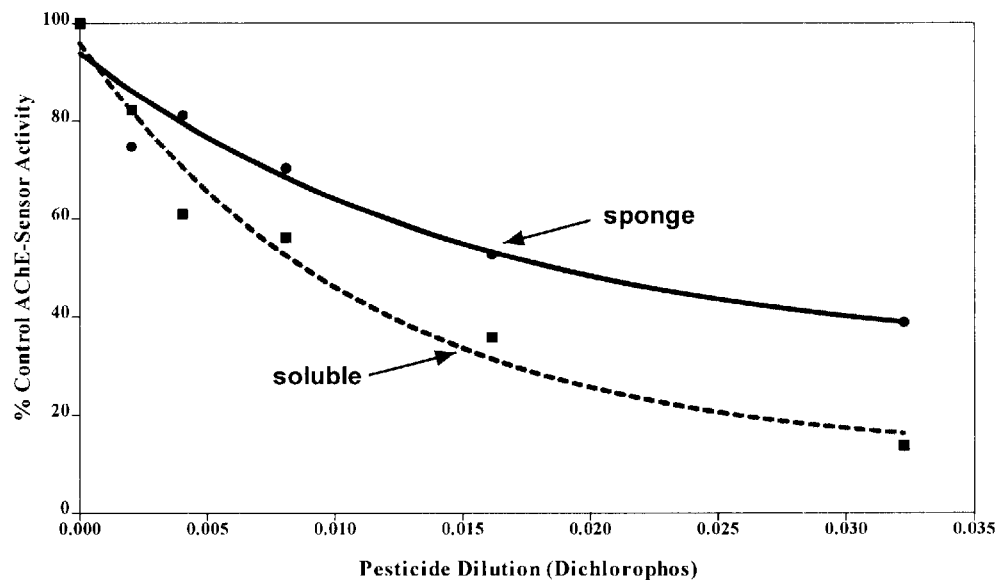
Figure 27A. Dose-dependent inhibition of Immobilized AChE sensor and soluble AChE to the Pesticide Dichlorophos
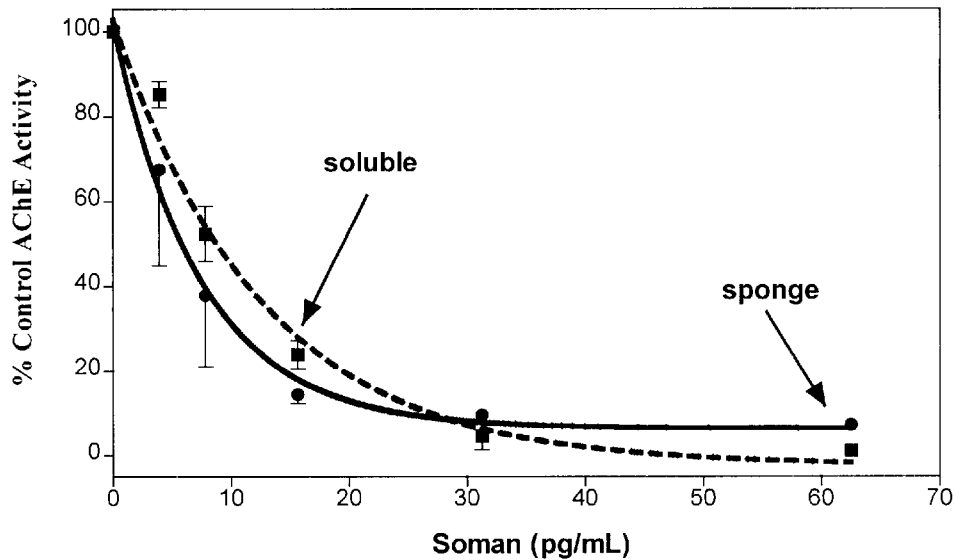
Figure 27B. Dose-dependent inhibition of Immobilized AChE (sensor) and soluble AChE to the organophosphate soman (GD)

DETOXIFICATION WITH SPONGES OR FOAMS CONTAINING PLURALITY OF ENZYMES AND ENCAPSULATED INDICATOR

This application claims benefit from prior Provisional Application Ser. No. 60/130,988, filed Apr. 26, 1999, incorporated herein by reference in its entirety.

TECHNICAL FIELD

This invention relates to materials, compositions, kits and methods for neutralizing, detoxifying or decontaminating equipment and/or personnel exposed to organophosphorus and organosulfur compounds.

BACKGROUND OF THE INVENTION

Methods for decontamination, neutralization and removal of chemicals, such as organophosphorus and organosulfur (OP) compounds, herbicides and insecticides, are known in the art. However, the compositions and devices utilized in the prior art methods have undesirable properties, such as corrosiveness, flammability, toxicity, difficulty in making and storing, and limited shelf-life.

For example, DS2, a standard decontamination agent. comprises 70% diethylenetriamine, 28% ethylene glycol monomethyl ether, amd 2% NaOH by weight. Although DS2 is effective, it is corrosive upon exposure to air. DS2 and any matter resulting from its use is classified and regulated as hazardous material. After an application, the DS2 must stand for 30 minutes before rinsing the treated area with water. Additionally, DS2 comprises a teratogen.

Some decontamination methods employ hypochlorite formulations which are corrosive and toxic and injure humans and sensitive tissues such as eyes. Other methods comprise incinerating the contaminated material and utilizing carbon filters to absorb the residual chemicals. Yet other methods utilize polymer beads or microemulsions which absorb the chemical and must be rinsed away. These methods are inherently dangerous, expensive and generate hazardous waste. Furthermore, as many of these compositions and compounds utilized degrade upon exposure to water and carbon dioxide, these compositions and compounds must be used the same day they are made.

Some in vivo methods employ cholinesterases in the presence of nucleophilic oximes to detoxify OP compounds. This enzyme bioscavenger approach is effective against a variety of OP compounds in rodents and nonhuman primates. For example, pretreatment of rhesus monkeys with fetal bovine serum acetylcholinesterase (FBS-AChE) or horse serum butyrylcholinesterase (Eq-BChE) confers protection against up to 5 $LD_{50}$ of soman, a highly toxic OP nerve agent. Although, the use of an enzyme as a single pretreatment drug for OP toxicity is sufficient to provide complete protection to an individual subject, a relatively large (stoichiometric) amount of the enzyme is required to neutralize the OP compound in vivo. Therefore, OP/enzyme stoichiometry is increased by combining enzyme pretreatment with oxime reactivation so that the catalytic activity of OP inhibited FBS-AChE is rapidly and continuously restored, and the OP compound is detoxified.

Clearly, a need for better methods and devices for neutralizing, detoxifying, decontaminating and cleaning materials, equipment and personnel exposed to OP compounds exists.

Thus, OP detoxifying compounds, devices and methods thereof, which allow the safe, effective and convenient detoxification and quantitative and qualitative determination of highly toxic compounds not possible by the prior art, have been developed. These environmentally friendly compounds, devices and methods are disclosed hereinbelow.

SUMMARY OF THE INVENTION

The present invention provides materials, compositions, kits and methods for neutralizing, detoxifying or decontaminating equipment and/or personnel exposed to OP compounds.

In one embodiment, the invention relates to a material comprising a mixture of enzymes and substrates for the removal, decontamination and neutralization of OP compounds including those directed against humans. The mixture of enzymes utilized comprises cholinesterases (ChEs) and/or OP hydrolases and reactivators, such as OP reacting compounds such as certain oximes like HI-6 and mono-bisquarternary oximes such as 2-PAM.

The material may comprise a flexible or rigid porous support. The porous support may be a polyurethane matrix or equivalent.

For example, the porous support may be a flexible sponge-like substance or like material, wherein the enzymes are secured by immobilization. Depending on the polyurethane prepolymer or substrate utilized, porous supports of varying degrees of flexibility and porosity may be obtained. The porous support may be formed into various shapes, sizes and densities, depending on need and the shape of the mold. For example, the porous support may be formed into a typical household sponge or a towelette. The preferred dimensions of the sponge are 1"×2"×8" to 2"×4"×8". The preferred dimensions of the towelette are 4"×4"×0.25" to 4"×4"×0.03125" to 14"×14"×0.0625". However, during large-scale synthesis, the dimensions of the initial immobilized enzyme product might be large. For example, approximately 4 feet by 8 feet rolls could be produced and sized as appropriate and described above.

The sponge-like support would be preferable for use on surfaces, including natural, synthetic and biological surfaces such as equipment, laboratory hardware, devices, skin and other delicate membranes, where decontamination of a rough or irregular surface is desired or where the prior art decontamination materials are incompatible with human tissue. For example, the materials may be used to clean and decontaminate wounds as it is non-toxic and the immobilized enzymes will not leach into a wound. Therefore, the sponges could be used to decontaminate civilians contaminated by a terrorist attack at a public event.

If an object and/or area to be neutralized or decontaminated comprises cracks, crevices, porous or uneven surfaces, a foam-like support is suitable. Application of small quantities may be done with a spray-bottle or spray can with an appropriate nozzle. Further, foam may be selected so that it can be dispensed into the opening of sensitive equipment or an orifice of a subject, such as the ear canal. If a large area is contaminated, an apparatus that dispenses a large quantity of foam may be utilized.

The foam-like support may dissipate after a period of time like shaving cream or it may cure into a stable and flexible sponge-like support. The dissipating foam may be applied on living subjects. The foam, which cures, may be applied around an object and contain the contamination within the foam. Once the foam cures, the object may be handled and moved without further exposure to the hazardous chemical.

When necessary, the material may also comprise a rigid and porous support. The rigid material can be ground into a powder and added to lotions, soaps and other liquids for application. Likewise, the flexible material, supra, may be appropriately treated to render it suitable for use in lotions, soaps and other liquids.

The material may also be in the form of a filter for neutralizing, detoxifying or decontaminating gases such as air. Additionally, the material may be in a form suitable for use as clothing or linings of clothing. Furthermore, the material may be used to decontaminate water by placing the material in water and then removing it from the water.

In another embodiment, the material can be color-coded according to the specific substance it may neutralize, detoxify or decontaminate. The color or color scheme could be selected to indicate enzymatic concentration, activity and/or remaining shelf-life or range thereof.

The materials of the invention may be placed in containers to complete decontamination of the OP compounds on the materials.

Other embodiments include the methods of using the instant materials for the quantitative or qualitative determination of hazardous compounds such as OP compounds.

As disclosed herein, one of ordinary skill in the art will appreciate the various materials and their uses as contemplated by the inventors. All of these forms may be appropriately combined with carbon for further absorption of OP compounds. The carbon may be embedded or incorporated within the porous support of the material or the carbon may be a layer, filter or other to be used in conjunction with the material. Additionally, a slow release form, such as a dry capsule, pellet, liposome or other, of a reactivating compound such as HI-6 may be embedded or incorporated within the porous support of the material.

A preferred embodiment of the invention comprises a material wherein AChE and/or BChE are simultaneously immobilized with OP hydrolases on or within the porous support during synthesis of the material. Preferably, the enzymes are immobilized through covalent linkages. The enzymes may be of prokaryotic or eukaryotic origin. These enzymes may be recombinant. The enzymes may be contained within the cell or cell free. Other enzymes capable of hydrolyzing hazardous chemicals such as OP compounds may be employed. Likewise, enzymes such as triesterase may be used for the decontamination of pesticides in a similar manner as herein described. Preferred enzymes are those that may be reactivated or directly hydrolyzed OP compounds.

In another embodiment, the invention relates to the process of making a material, for the removal, decontamination or neutralization of hazardous chemicals such as OP compounds, comprising a mixture of enzymes immobilized on a porous support. In this embodiment, a mixture of enzymes and a prepolymer are gently and evenly mixed together with minimal degradation of the biotype component so that the resulting immobilized enzyme may effectively decontaminate, neutralize or detoxify an amount of an OP compound. The device utilized, folds the components into one another. This is a low shear process. During synthesis of the material by prior art methods, for example a mixing drill, the enzymes utilized are subjected to fluid forces or shear stress. Use of a device that gently folds the components into one another greatly reduces these fluid forces or shear stress, and is the preferred device for enzymes, specifically enzymes that are sensitive to the high shear forces of the drill mixing device. Additionally, use of additives such as surface-acting polymers, e.g. P-65, or low concentrations of glycerol protects against enzyme denaturation induced by shear forces. The surface-acting polymers also gives appropriate consistency and absorbency of the solid support.

In a preferred process of making the material, a two chamber apparatus is utilized. One chamber contains a mixture of enzymes and the other chamber contains the prepolyrmer. The mixture of enzymes and the prepolymer are simultaneously extruded at a 1:1 ratio and mixed. Preferably, the mixture of enzymes and the prepolymer are rapidly and evenly extruded through a static mixing stator which gently and evenly mixes the enzymes and prepolymer. A preferred low shear device is a double chamber syringe and a static mixing stator typically used to mix viscous polyurethanes or epoxy glues. The size of the apparatus may vary depending on need. It may be pocketsize for use in the field by soldiers. Alternatively, the apparatus may be suitable for large-scale production and/or decontamination of a large objects or area. The low shear mixing device more than doubles the resultant AChE or BChE immobilized enzyme activity when compared to an identical mixture prepared with the high shear device.

The invention further relates to various materials, methods and devices for reactivating the enzymatic activity of the material. These materials, methods and devices will allow a person to use the decontamination material of the invention for several separate uses and/or for a single and continuous use, which would normally require several decontamination materials but for reactivation of the enzymatic activity of the immobilized enzymes. Additionally, these materials, methods and devices allow for complete decontamination and/or neutralization of excess OP compounds absorbed by the porous support but did not react with the immobilized enzymes. These methods and reactivation materials employ substrates and/or oximes, to reactivate the catalytic activity of the OP inhibited and immobilized enzymes.

The invention further relates to various materials and additives that are added to the embodiment to aid in the removal and decontamination of organophosphates from surfaces such as cracks, crevices, porous or uneven surfaces such as clothes and biological surfaces that readily absorb the organophosphates or pesticides such as skin. The additives are used in conjunction with the sponge material and may be incorporated within the porous support of the material. The additives may be in a dry or liquid form, and may be organophosphate solubilizing compounds such as triacetin or tetraglyme, or oximes, which both aid in decontaminating and reactivating enzymes.

Another embodiment of the invention relates to a variety of kits. These kits contain the sponge containing a plurality of enzymes needed for the decontamination of organophosphorus and/or sulfur compounds. Also included may be materials which would facilitate or be deemed necessary for the decontamination process. Kits may also include polymeric materials and enzymes if the foam is transient in nature, e.g. the prepolymer, a stable enzyme mixture and a low shear apparatus for making an organophosphorus and/or organosulfur decontamination foam. These kits may also include the indicators for both quantitative or qualitative detection of OP compounds and means for transmitting results to a central collection point, e.g. computer, satellite uplinks, radio relays, handheld battery operated measuring devices, etc. For example, one may quantitatively analyze the OP compounds by using a handheld battery operated measuring devices and interfacing with a computer to calculate reaction rates which rates may be relayed to a central collection point. The kits may contain items to facilitate the use of the device, e.g. instructions, containers, test tubes, etc.

DESCRIPTION OF THE DRAWINGS

This invention is further understood by reference to the drawings wherein:

FIG. 1A illustrates the modeled surfaces of acetylcliolinesterase, butyrycholinesterase and phosphotriesterase.

FIG. 2 shows a cured material.

FIG. 3 schematically illustrates the specific reaction of the enzymes with prepolymer.

FIG. 4 shows the linear correlation between the amount of BChE added during synthesis of the material and the amount of BChE in the final material.

FIG. 5 shows the increasing amounts of BSA added during synthesis to a constant amount of AChE and TDI polymer.

FIG. 6 illustrates that the materials maintained enzymatic stability for more than 3 years at 4° C. and more than 12 months at 25° C. and 45° C.

FIG. 7 shows that the material maintained enzymatic activity after consecutive washes.

FIG. 9 illustrates the pH range of soluble and immobilized AChE.

FIG. 10 shows the relative activities of co-immobilized ChEs and OPHs.

FIG. 12 schematically illustrates alternate schemes for detecting ChE activity.

FIG. 13 is a model of a carbon electrode with immobilized ChE.

FIG. 14 illustrates how F⁻ reverses the reaction between an OP compound and ChE.

FIG. 15 illustrates how oximes may reactivate alkylphosphorylated ChE.

FIG. 16A illustrates the enzyme activity of immobilized FBS-AChE. FIG. 16B illustrates the enzyme activity of immobilized Eq-BChE.

FIG. 17 represents inhibition of foam-immobilized FBS-AChE by DFP and reactivation by HI-6.

FIG. 18 represents inhibition of foam-immobilized Eq-BChE by DFP and reactivation by TMB4.

FIG. 20A shows the pH profile of soluble and immobilized choline oxidase. FIG. 20B shows substrate concentration dependent curve for soluble and polyurethane coupled choline oxidase.

FIG. 21A shows temperature profile of immobilized and soluble AChE. FIG. 21B shows temperature profile of immobilized and soluble BChE.

FIG. 23 shows inhibition of AChE-sensor by the organophosphate MEPQ, which is not reversed by washing in water or buffer.

FIG. 24A shows protection afforded by sponge with tetraglyme additive. FIG. 24B shows protection afforded by sponge with HI-6 additive. FIG. 24C shows protection afforded by sponge with 2-PAM additive.

FIG. 26A shows AChE-sensor activities after continuous incubation at 25° C. at different pHs. FIG. 26B shows BChE-sensor activities after continuous incubation at 25° C. at different pHs. FIG. 26C shows AChE-sensor activity after continuous exposure to Chesapeake Bay (Brackish) water at 25° C. FIG. 26D shows AChE-sensor activity after continuous exposure to Allegheny River (Fresh) water at 25° C. FIG. 26E shows sensitivity of M272 ticket to aqueous conditions (Chesapeake Bay brackish water). FIG. 26F shows sensitivity of M272 ticket to aqueous conditions (50 mM phosphate buffer, pH 8.0).

FIG. 27A shows dose-dependent inhibition of immobilized AChE sensor and soluble AChE to the pesticide dichlorophos. FIG. 27B shows dose-dependent inhibition of immobilized AChE (sensor) and soluble AChE to the organophosphate soman (GD).

DETAILED DESCRIPTION OF THE INVENTION

Figure 1B:
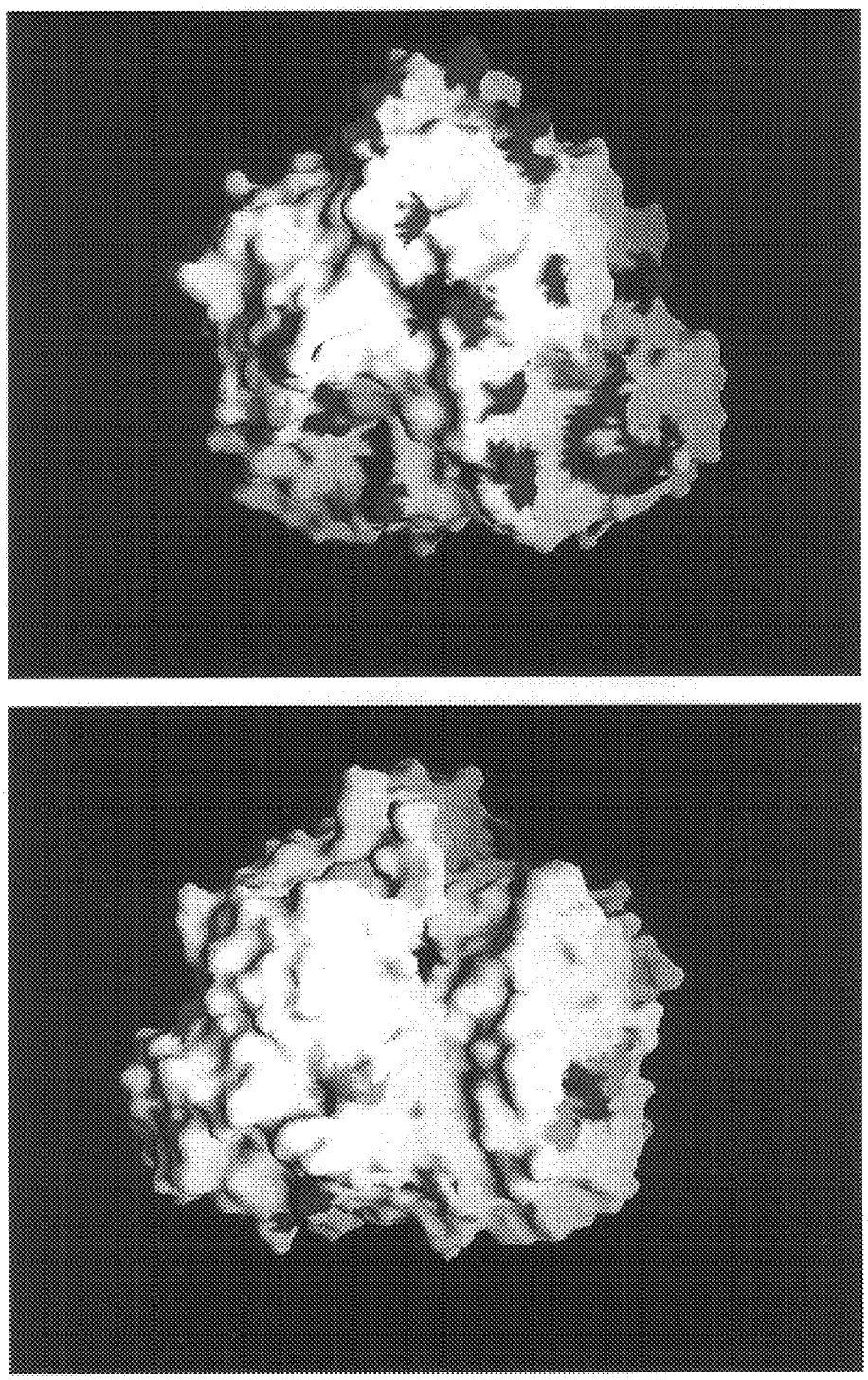
FIG. 1B illustrates the modeled surfaces of laccase.

Enzymes have been incorporated in hypo-based urethane foam during polymer synthesis. See U.S. Pat. No. 4,342,834. Hypoprepolymer is synthesized from a reaction of polyether (or polyester) polyol with isocyanates in the presence of cross-linking agents. See Havens, P. L., et al., *Ind Eng Chem Res* (1993)32:2254–2258; U.S. Pat. No. 4,137,200; LeJeune, K. E., et al., *Biotechnology and Bioengineering* (1999) 20;62(6):659–665. Synthesis is initiated by bringing water molecules into contact with isocyanate groups present within the polyurethane prepolymer.

A two-step procedure occurs from this point. Isocyanates react with water to form an unstable carbonic acid, which in turn degrades to an amine yielding $CO_2$ that gives the porous support lift and enables it to rise. The amines readily react with isocyanate groups, leading to production of urea type linkages. Since the enzyme contains multiple functional groups, such as amines and hydroxyls that can react with isocyanates, the enzyme becomes an integral part of the porous support during synthesis. Significant quantities of enzyme can link to the porous support without disrupting the progress of polymer synthesis. The reaction occurring during the polymer synthesis is shown below.

1. $CO_2$ Evolution:

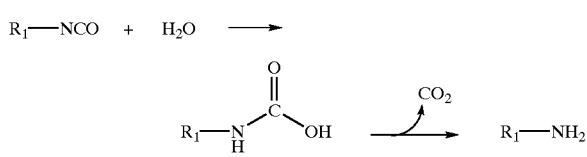

2. Urea Linkage:

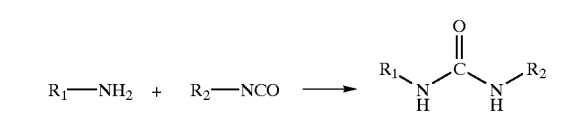

3. Amine Group Enzyme Immobilization:

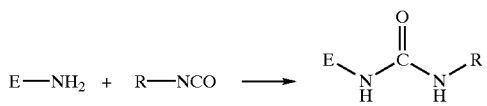

4. Hydroxyl Group Enzyme Immobilization:

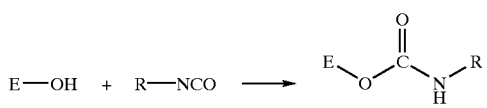

The following list of enzymes and chemicals are examples of those suitable for use in the instant invention:

Acetylcholinesterase (AChE);
Butyrylcholinesterase (BChE);
Pseudocholinesterase;
Organophosphate hydrolases (OPH);
Organophosphate acid anhydrase(OPAA);
Phosphotriesterase;
*Pseudomonas diminuta* bacterial OPH (paraoxonase);
Laccases;
Pralidoxime chloride (2-PAM);
7-(methoxyphosphinyloxy)-1-methylquinolium iodide (MEPQ);
Diisopropyl fluorophosphate (DFP);
Acetylthiocholine iodide (ATC);
S-butyrylthiocholine iodide (BTC);
5,5'-dithio-bis(2-nitrobenzoic acid) (DTNB);
N,N'-trimethylene bis(pyridinium-4-aldoxime) dibromide (TMB4); and
1-(2-hydroxyiminomethyl-1-pyridinium)-1-(4-carboxyaminopyridinium)dimethylether hydrochloride (Hi-6).

By using mammalian cholinesterases such as FBS-AChE or Eq-BChE rather than Eel cholinesterase as is found in the M272 ticket (currently used to detect organophosphate compounds), the immobilized enzyme will display the same sensitivity to OPs that mankind is susceptible to now, or any new or novel OPs that might be produced in the future against mankind. Other enzymes capable of hydrolyzing hazardous chemicals such as OP compounds may be employed, for example laccase. Additionally, other OP hydrolyzing enzymes would ensure rapid and complete destruction of any toxic intermediates (for example, phosphoryloximes) that might be generated during the decontamination process.

The following examples are intended to illustrate but not to limit the invention.

EXAMPLE 1

Determination of Possible Enzyme Interference

As polyether prepolymer derived from tolyl diisocyariate (TDI), reacts most favorably with free aliphatic amines such as lysine and arginine present on the surface of the ChEs (or any protein) to become a permanent cross-linked part of the material, computer aided molecular modeling of the enzymes was performed to highlight the available amino groups on the surface of each enzyme, and to determine whether the coupling of these groups to a porous support would interfere with enzymatic function. This may be performed on every enzyme for which its crystal structure is known, or enzymes which may be modeled by homology.

FIG. 1A illustrates the modeled surfaces of acetylcholinesterase, butyrycholinesterase and phosphotriesterase and shows the lysine and arginine residues on the surface of the ChEs which are available for coupling to the prepolymer. This was generated by Insight II, molecular modeling software, by Biosym Technologies. Based on the molecular modeling, there are at least one lysine and 29 arginine water-accessible residues on the surface of FBS-AChE to couple to the porous support, while 26 lysine and 26 arginine residues were modeled for equine-BChE. The majority of the lysine and arginine residues were found on the backside of the ChEs, and only a few are found on the side of the enzyme where the catalytic site gorge is located. The rim and the catalytic site gorge opening of both AChE and BChE appeared to be essentially devoid of lysine and arginine. Therefore, coupling these enzymes to the porous support should have minimal effect on the entrance of substrate, inhibitors such as OPs, or reactivators such as oximes which includes mono-bisquarternary oximes, release of products of catalysis to and from the active site, and the kinetic rates of the enzymes. Similarly, a model of the surface of laccase (FIG. 1B) is shown with available residues to couple covalently to the prepolymer.

EXAMPLE 2

Synthesis of an Enzyme Bound Polyurethane Material

A typical synthesis of the material comprises mixing enzymes in phosphate buffer containing 1% (final concentration) surfactant with prepolymer. Polyether prepolymer derived from tolyl diisocyanate (TDI), Hypol prepolymer TDI 3000 (Hampshire Chemical, Lexington, Mass.), and Pluronic P-65 surfactant (BASF Specialty Chemicals, Parsippany, N.J.) were used. The 2-phase system is mixed and placed into a suitable mold and left to cure. FIG. 2 shows a cured material which comprises a sponge-like support.

FIG. 3 schematically illustrates the specific reaction of the enzymes with prepolymer. Synthesis begins when $H_2O$ molecules react with the isocyanate groups present within the polyurethane prepolymer. Isocyanate reacts with the water to form an unstable carbonic acid, which degrades to an amine yielding $C_2$. The $CO_2$ causes the polymer to rise and become porous, and simultaneously the amines readily react with the isocyanate groups leading to urea linkages.

Since the ChE contains amines that are on the surface and available to react with the isocyanate groups, they can become an integral part of the polyurethane support during synthesis. There is no significant entrapment of the enzyme in the material as found with cyclodextrins, or physical adsorption of the enzymes, as observed with activated carbon. The inclusion of a surfactant such as Pluronic P-65 at about 1% final concentration controls the final structure and absorption potential of the material.

To create a material comprising a porous polyurethane support, approximately 30 mL of 50 mM phosphate buffer, pH 8.0, containing P-65 surfactant buffer, was placed in a 600 mL plastic beaker. 3 to 5 mL of either purified FBS-AChE (7500 units) or purified Eq-BChE (5000 units) was added, followed by approximately 40 gm of Hypo 3000 prepolymer (tolyl diisocyanate). The two-phase system was mixed and the material was allowed to expand for 10 min, extruded from the container. The material was washed thoroughly with 50 mM phosphate buffer, pH 8.0, dried and stored in a zippered bag at 4° C. for future use.

EXAMPLE 3

Characteristics of Synthesized Material

Approximately 20–90% of the enzymes were covalently linked to the porous support through free amino- or hydroxyl groups. This was determined by the presence of enzyme in first and second washes of the material.

Since the enzymes can be attached at multiple points they become a part of the cross-linked polymer support. The cross-linked polymer support imparts considerable stability to the bound enzymes. A large quantity of enzyme can be incorporated into a small polyurethane support, thereby rendering the cross-linked polymer support a highly effective material for decontamination.

A. Enzymatic Activity

Five samples of materials containing FBS-AChE and five samples of materials containing Eq-BChE, ranging in weight from 1 to 40 mg, were suspended in 2.8 mL of 50 mM phosphate buffer, pH 8.0, and assayed using the method of Ellman. See Ellman, G. L., et al., (1961) *Biochem Pharmacol.* 7:88–95. A linear correlation was found between the weight of the sponge and enzyme activity for both FBS-AChE and Eq-BChE immobilizations. See FIGS. 16A and B. The linear correlation between the weight of the material and enzyme activity indicates a uniform immobilization of ACHE or BChE throughout the material.

The material was washed with either 50 mM phosphate buffer, distilled water, or 10 mM ammonium bicarbonate without affecting substrate hydrolysis. Therefore, the mixing of prepolymer, surfactant, and enzyme in situ at 22° C. yields a useful and effective material retaining about 50% of the original activity of soluble ChE.

B. Protein Loading Capacity

The material has a significantly higher loading capacity for ChEs such as BChE or AChE. The final activity of the BChE immobilized in the material could be increased by adding larger quantities of enzyme during synthesis. See FIG. 4. When nonspecific protein (bovine serum albumin, BSA) was added to a constant amount of purified ACHE, there was no reduction in ChE activity. See FIG. 5. Thus, higher potency materials may be synthesized with additional proteins, enzymes and other ChEs. Additionally, materials effective against a diverse array of OP compounds may be readily synthesized by with combinations of multiple enzymes or a plurality of enzymes.

C. Enzymatic Stability

As illustrated by FIG. 6, the immobilized ChE and OP hydrolase maintained enzymatic stability for more than 3 years at 4° C., and more thin 12 months at 25° C. and 45° C., respectively. If the material is frozen in liquid nitrogen, most of the original activity remains. TDI imparts remarkable stability to the immobilized ChE; about 50% of the original activity of the immobilized AChE and 20% of the activity of the immobilized BChE remained after 16 hours at 80° C., conditions under which the soluble enzymes would exhibit no activity. The ChE materials can be exhaustively dried under vacuum at 22° C. and then rehydrated without loss of enzyme activity. When AChE or BChE materials were exhaustively washed and assayed for activity, the wash and assay cycle repeated more than twenty times over three days, no decrease in activity occurred. See FIG. 7. This indicates that the material may be used repeatedly.

These results also demonstrate that the ChEs are covalently cross-linked in the porous support and that the ChEs will not leach out to skin, water, or equipment. Therefore, once the immobilized enzymes bind an OP compound the OP is removed from the surface requiring decontamination.

D. Kinetic Constants

TABLE 1

Time-Dependent Inhibition of ChEs by MEPQ

| ChE | Enzyme Form | Bimolecular rate constant ($M^{-1}$ $min^{-1}$) ± SD |
|---|---|---|
| FBS-AChE | soluble | 1.59 ± 0.52 × $10^8$ |
|  | coupled to sponge | 1.00 ± 0.28 × $10^8$ |
| Equine-BChE | soluble | 4.15 ± 0.78 × $10^7$ |
|  | coupled to sponge | 4.21 ± 2.00 × $10^7$ |

The number of active sites of either the immobilized or soluble ChEs was determined by titration with the organophosphorus compound MEPQ, 7-(methylethoxyphosphinyloxy)-1-methylquinolinium iodide. The bimolecular rate constants for the inhibition of AChE material and BChE material and the respective soluble enzymes by MEPQ at 25° C. showed that there was no significant difference between the soluble and covalently bound enzymes. See Table 1.

These results demonstrate that the immobilized and soluble forms of ChEs interact with the OP compounds similarly. Therefore, enzymatic activity assays which are generally available and known in the art may be used.

Figure 8:
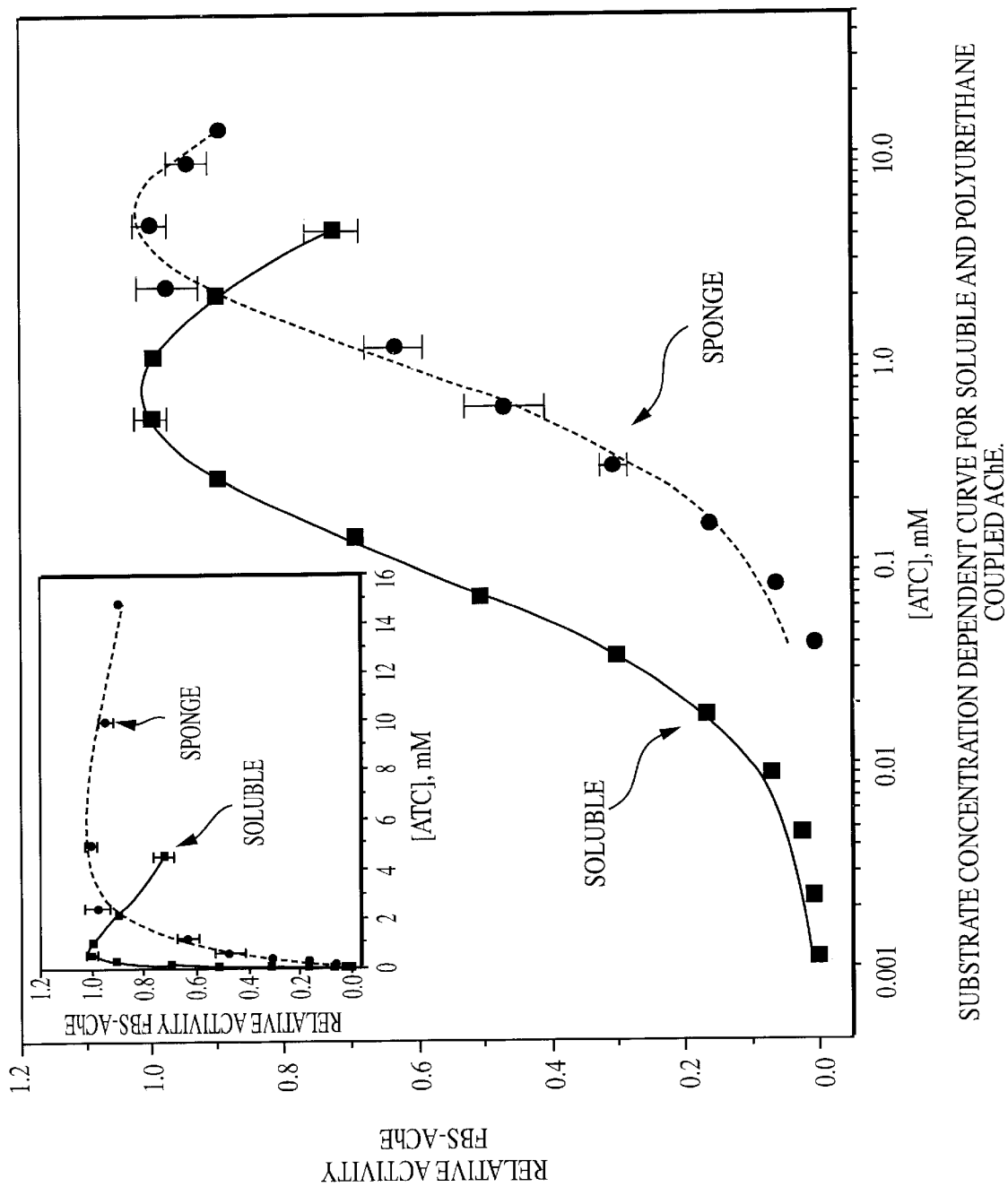
FIG. 8 shows a substrate concentration dependent curve for soluble and polyurethane coupled AChE.

An initial rates method using a modified Ellman's assay was used to determine the parameters $K_m$, $k_{cat}$, and $k_{cat}/K_m$ for immobilized and soluble AChE and BChE. The number of active sites of either the coupled or soluble ChEs was determined by titration with MEPQ. As shown in Table 2 and FIG. 8 for AChE, the $K_m$ values for the immobilized ChEs were about 10-fold greater than the corresponding soluble enzymes, and the $k_{cat}$ values were less dramatically affected. The combined effects on affinity for substrate and $k_{cat}$ resulted in approximately a 20 to 50-fold decrease in acylation ($k_{cat}/K_m$). Interestingly, while soluble BChE lacked substrate inhibition, immobilized BChE yielded substrate inhibition. These results suggest that covalent binding of surface residues of ChEs to the porous support changed some properties of the active site region of the bound enzymes directly or indirectly.

TABLE 2

Kinetic parameters for soluble and polyurethane coupled ChEs.

| Enzyme | Form | Substrate inhibition | $K_m$ (mM) | $K_{ss}$ (mM) | B | $K_{cat}$ ($min^{-1}$) | $K_{cat}/K_m$ ($M^{-1}min^{-1}$) |
|---|---|---|---|---|---|---|---|
| FBS-AChE | Soluble | yes | 0.119 | 18 | — | 2.8 × $10^5$ | 2.5 × $10^9$ |
|  | immobilized | yes | 1.090 | 22 | — | 5.9 × $10^4$ | 5.4 × $10^7$ |

TABLE 2-continued

Kinetic parameters for soluble and polyurethane coupled ChEs.

| Enzyme | Form | Substrate inhibition | $K_m$ (mM) | $K_{ss}$ (mM) | B | $K_{cat}$ (min$^{-1}$) | $K_{cat}/K_m$ (M$^{-1}$min$^{-1}$) |
|---|---|---|---|---|---|---|---|
| Equine-BChE | Soluble | no | 0.127 | 1.5 | 1.8 | $3.1 \times 10^4$ | $2.4 \times 10^8$ |
|  | immobilized | yes | 1.200 | 16 | — | $1.8 \times 10^4$ | $1.5 \times 10^7$ |

Determined in 50 mM phosphate, pH 8 at 25° C. using an initial rates method.
Calculated from $V_{max}$ and the active site concentration of ChE that was determined by MEPQ titration.
Values were calculated[2] using modified Haldane equations, and the special case where b = 0.
The best fit between the two was determined using an F test, where significance was defined as $p < 0.05$.

Figure 19A:
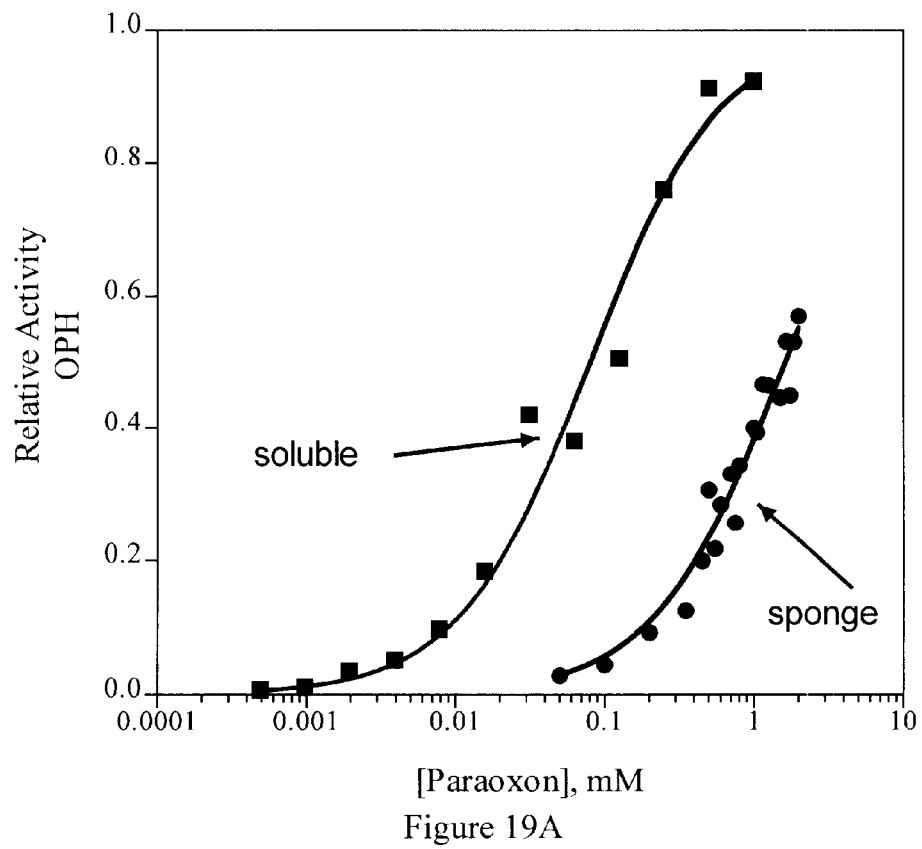
FIG. 19A shows about a 10-fold increase in $K_m$ beciuse a shift to the right is also observed in the immobilized (sponge) form when determined using the substrate paraoxon. On the other hand.
Figure 19B:
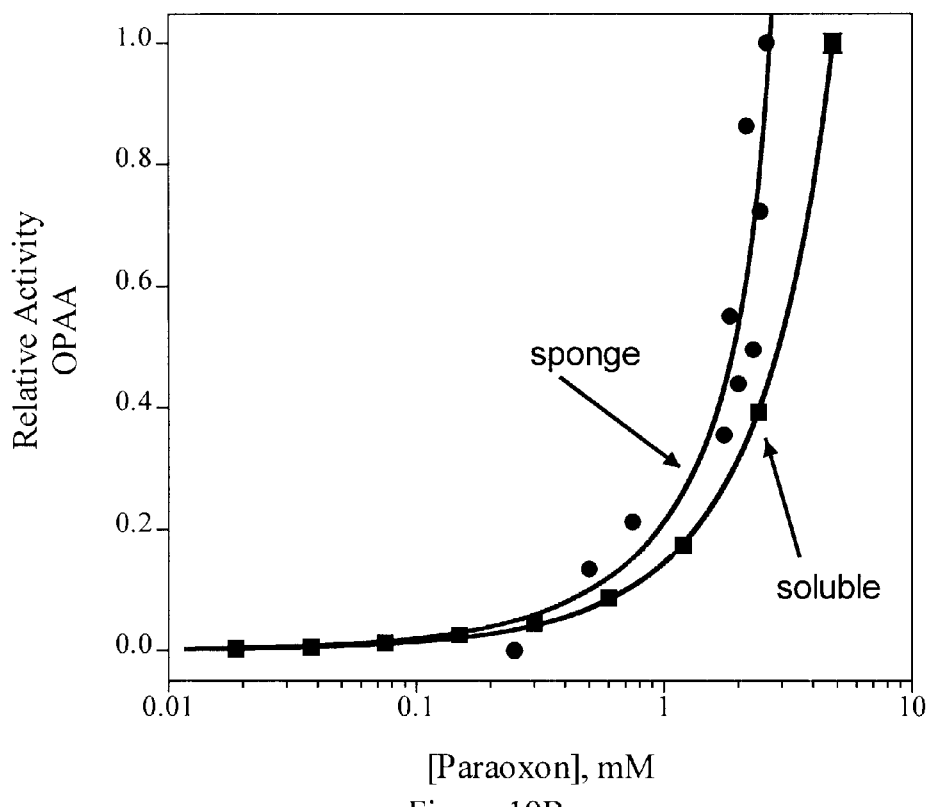
FIG. 19B shows shows little change in $K_m$ for the substrate paraoxon, with OPAA (derived from Alteromonas).

Generally, immobilized cholinesterases or OP hydrolyzing enzymes exhibit between the same to 10 fold greater $K_m$ values than the corresponding soluble enzymes. In addition to the cholinesterases, OPH (derived from Pseudomonas diminuta, FIG. 19A) shows about a 10-fold increase in $K_m$ because a shift to the right is also observed in the immobilized (sponge) form when determined using the substrate paraoxon. On the other hand, OPAA (derived from Alteromonas, FIG. 19B), shows little change in $K_m$ for the substrate paraoxon.

$K_m$ Determination of immobilized and soluble choline oxidase:

The $K_m$ of the soluble and immobilized forms (sponge) of choline oxidase are observed to be similar since there is little shift in the substrate curve, as shown by FIG. 20B, indicating that this enzyme is not only very suited to immobilization, but also for co-immobilization with the cholinesterases. The observed $K_m$ for soluble and sponge are 2.5 and 6.7 mM, respectively.

E. pH of Soluble and Immobilized Enzymes

The pH profiles of immobilized and soluble AChE are identical and the enzymes exhibit activity throughout the broad pH range of 7–8.5. See FIG. 9. Since the pH profiles of soluble cholinesterases, OP hydrolases and choline oxidases have optimal activities in this same pH range, the materials may be optimized and diversified by employing a plurality of these multiple enzymes immobilized on or within a porous support.

FIG. 20A: The pH profile of soluble and immobilized choline oxidase. Compare with FIG. 9, the pH profile of soluble and immobilized acetylcholinesterase Temperature Dependent Activity of Soluble Cholinesterases and Sensor (Immobilized) Cholinesterases The sensors containing immobilized AChE or BChE exhibited almost identical temperature dependent activity when compared to their soluble counterparts (FIGS. 21 A and B). However, as shown in FIG. 6, the immobilized enzymes are more resistant to the denaturing conditions of elevated temperatures for extended periods, while the soluble enzymes are not. The immobilized enzymes are also resistant to freezing in liquid nitrogen. These profiles indicate that at cold temperatures, the sensors could be warmed by body heat or an external source to increase the reaction rates.

EXAMPLE 4

Immobilization of a Plurality of Enzymes

ChEs were co-immobilized with bacterial OP hydrolase (OPH$_B$) and/or rabbit serum OP hydrolase (OPH$_R$). There was no reduction in the enzymatic activities of AChE or BChE co-immobilized with OPH as compared to the enzymatic activities of each of these enzymes individually immobilized. See FIG. 10. Additionally, there was no reduction in the enzymatic activity of co-immobilized OPH. Therefore, a plurality of enzymes, which each enzyme differentially reacts with various OP compounds, may be selected and utilized in a material to create a decontamination material effective against a wide range of OP compounds.

EXAMPLE 5

Rapid Mixing Synthesis

Figure 11A:
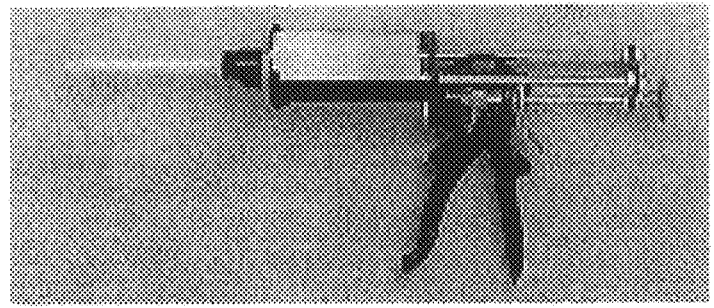
FIGS. 11A and B show a version of a manual mixing gun and a disposable mixing stator.
Figure 11B:
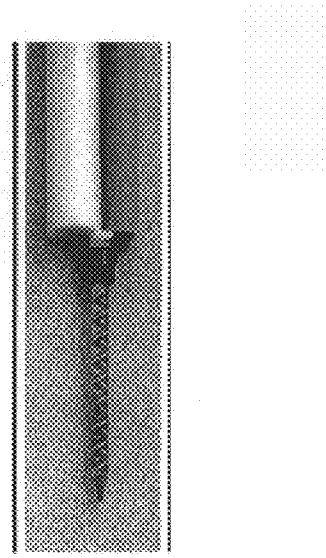

By utilizing a method of syntheses modified from the adhesive industry (CPA, Greenville, R.I. 02828) shear forces which decrease enzymatic activity are reduced. See FIGS. 11A and B. In this method, the enzyme is not in an organic buffer as required in some immobilization techniques. This results in less air-induced shearing, thereby maintaining enzymatic activity. This method is also simple to conduct, rapid and reproducible. The low shear mixing device more than doubles the resultant AChF and/or BChE immobilized enzyme activity when compared to an identical mixture prepared with the high shear device such as a mixing drill. See Table 3.

TABLE 3

| Technique | AChE Activity U/mg |
|---|---|
| High shear mixing drill | 0.100 |
| Low shear 2-chamber device | 0.270 |

EXAMPLE 6

Inhibition of Immobilized FBS-BChE with DFP and Reactivation with HI-6

100 mg samples of immobilized FBS-AChE were incubated with varying concentrations of DFP in 2 mL of 50 mM phosphate buffer, pH 8.0, for 1 hour at 25° C. In parallel experiments, 1 mM HI-6 was added to the same amount of material and DFP. Residual DFP in the samples was measured by adding a 0.5 mL aliquot of the reaction mixture to 0.5 mL of a fresh 1 U/mL solution of FBS-AChE, incubating for 1 hour, and assaying 10 µl aliquots using the Ellman procedure. The results are shown in FIG. 17.

The inhibition of FBS-AChE activity by DFP was proportional to the stoichiometric amount of DFP added to the foam suspended in buffer. The presence of 1 mM HI-6 nearly completely prevented enzyme inhibition by DFP. This indicates that immobilized FBS-AChE may be repeatedly reused

EXAMPLE 7

Inhibition of Immobilized Eq-BChE with DFP and Reactivation with TMB4

50 mg samples of immobilized Eq-BChE were incubated with varying concentrations of DFP in 2 mL of 50 mM phosphate buffer, pH 8.0, for 18 hours at 25° C. In parallel experiments, 1 mM TMB4 was added to the same amount of material and DFP. Residual DFP in the samples was determined by adding a 0.5 mL aliquot of the reaction mixture to 0.5 mL of a fresh 1 U/mL solution of Eq-BChE, incubating for 1 hour, and assaying 10 μl aliquots using the Ellman procedure.

TMB4 was used as a reactivator instead of HI-6, since TMB4 is a more efficient reactivator of inhibited Eq-BChE than is HI-6. These results are shown in FIG. 18. As in Example 6, the foam-bound Eq-BChE may be repeatedly reused after reactivating the enzyme with an oxime solution such as TMB4. FIG. 15 illustrates how oximes may reactivate alkylphosphorylated ChE activity.

EXAMPLE 8

Determination of Enzymatic Activity

FIG. 12 illustrates a variety of methods for determining presence of immobilized AChE and/or BChE and/or the effectiveness of a material. In the following examples, the material is first exposed to OP compounds and then qualitative and/or quantitative analysis may be performed. Qualitative analysis may be visually performed by utilizing visible chromogens and/or chemiluminescent chromogens. Quantitative analysis may be performed by using handheld devices, which measure amounts of fluorescence, chemiluminescence, or visible chromogens. Alternatively, the amount of $H_2O_2$ generated may be used to determine the effectiveness of the material.

For evaluating the presence of immobilized AChE and/or BChE in a material, a modified Ellman method in an aqueous phosphate buffered environment containing either acetylthiocholine for AChE or butyrylthiocholine for BChE as substrates may be conducted. If immobilized AChE and/or BChE are present, an intense yellow color will result from the reaction and may be spectrophotometrically monitored at 412 nm. For determining the presence of immobilized OP hydrolases in a material, diethyl p-nitrophenylphosphate may be used as the substrate and the reactions may be monitored at 500 nm. The Ellman and OP hydrolase assays produce a yellow chromogen if the enzyme is present, and no color if the enzyme is absent. Alternatively, 2,6-dichloroindophenyl acetate may be used as the substrate will remain a red color if the enzyme is absent and will turn blue (2,6 dichloroindophenylate) if the enzyme is present.

For fluorescent determination of the presence of an immobilized enzyme, the substrate may be either 1-methyl-7-acetoxyquinolinium iodide. In the presence of an enzyme, a highly fluorescent compound, 1-methyl-7-hydroxyquinolinium iodide, will result, i.e. 405 nm/em 505 nm. Alternatively, fluorogenic majleimide N-(4-(7-diethylamino-4-methyl-coumarin-3-yl)phenyl)-maleimide which condenses with the thiol formed from acetyl- or butyryl-thiocholine hydrolysis by ChEs, may indicate the presence of the immobilized enzyme, i.e. 390 nm/em 473 nm.

For chemiluminescent analysis, a ChE substrate and or benzoylcholine, choline oxidase, peroxidase and luminol are utilized.

Electrodes may be used to detect the presence and effectiveness of a plurality of immobilized enzymes in a material with the use of a plurality of substrates such as ChEs, choline oxidase, and peroxidase.

EXAMPLE 8

Inhibition of Immobilized AChE with the Organophosphate MEPQ and Detoxification of the MEPQ and Reactivation of the Immobilized Enzyme in the Presence of HI-6

Figure 22:
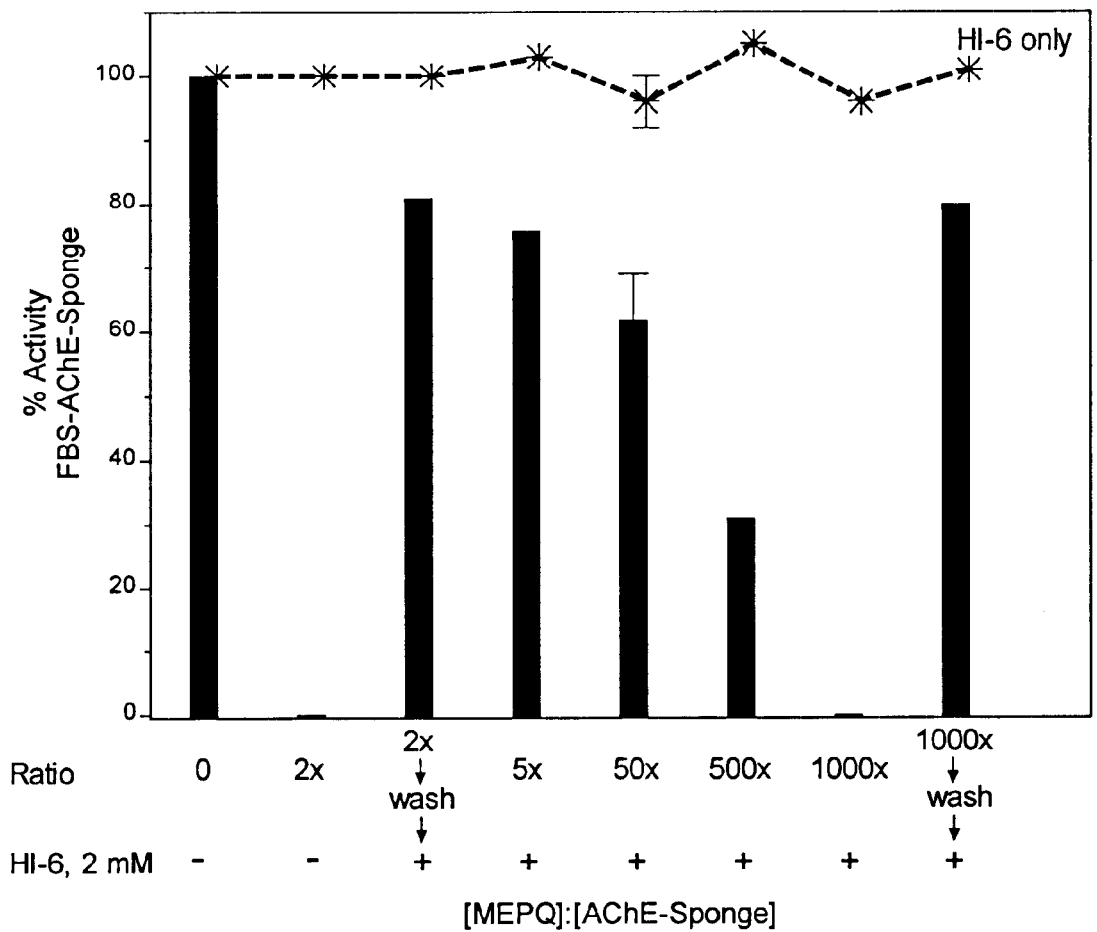
FIG. 22 shows that only at very high ratios of organophosphate (1000-fold molar excess) is the process of binding, reactivation, and detoxification not complete. However, fresh HI-6 can restore most of the original activity once again.

50 mg samples of immobilized acetylcholinesterase were incubated with varying concentrations of MEPQ in 2 mL of 50 mM phosphate buffer, pH 8.0 at 25° C. for 1 hr. In the absence of oxime HI-6, the sponge soaks up the MEPQ and is inactivated. Addition of HI-6 reactivates the sponge's activity, and the MEPQ is detoxified, and most of the original activity of the sponge returns. Only at very high ratios of organophosphate (1000-fold molar excess) is the process of binding, reactivation, and detoxification not complete. However, fresh HI-6 can restore most of the original activity once again. See FIG. 22.

EXAMPLE 9

50 mg samples of immobilized FBS-AChE were incubated with twice the stoichiometric ratio of the organophosphate MEPQ in 2 mL of 50 mM phosphate buffer, pH 8.0 for 10 min or 30 min at 25° C. Within the shortest time period measured, the sensor indicates inhibition. Furthermore, the sensor can be washed in water or buffer without reversing the inhibition by the organophosphate. See FIG. 23.

EXAMPLE 9

Diversified Material Comprising Multiple Immobilized Enzymes

Materials comprising cholinesterases, OP hydrolases; and enzymes which hydrolyze other OPs may be covalently immobilized on, within or encapsulated in a porous support to form a material for neutralizing, detoxifying or decontaminating equipment and/or personnel exposed to a diverse array of OP compounds. For example, since serum OP hydrolase from rabbit exhibits high activity with sarin, but not with soman, rabbit OPH and OPH from another source may be co-immobilized within a porous support to form a material useful for neutralizing, detoxifying or decontaminating both sarin and soman.

Additionally, since the enzymes from several species of halophilic and Alteromonas bacteria have considerable variation in enzymatic activity towards organophosphorus compounds, a plurality of these enzymes may be immobilized on or within the porous support. For example, since OPH from *A. undi* displays higher enzymatic activity against soman with respect to sarin and/or tabun, OPH from *A. undi* and OPH from another source having high activity against sarin and tabun may be used. Furthermore, a plurality of OP hydrolases, ChEs, laccases an(ior mediators of laccases and mutations thereof may be used for making a material effective against a broad range of OP compounds.

Tables 4 and 5 outline a few enzymes that may be used against given OP compounds.

TABLE 4

| | Relative activity of enzyme | | | |
|---|---|---|---|---|
| OXYGEN | AChE or BChE | Rabbit OPH | *Alteromonas undi* | Laccase |
| Sarin | Inhibited | ++ | + | − |
| Soman | Inhibited | − | +++ | − |
| Tabun | Inhibited | − | + | − |
| VX | Inhibited | − | − | ++ |

−, not tested or not hydrolyzed

TABLE 5

| Potential multiple immobilized enzymes | | |
|---|---|---|
| Enzyme type and origin | Distinguishing characteristics | References |
| AChE, BChE | Inhibited by OPs | 1, 2 |
| Laccase | Hydrolyzes VX preferentially with mediator | 21 |
| OPH | | |
| Human serum | Hydrolyses tabun, VX poorly | 13 |
| Rabbit serum | Hydrolyses sarin preferentially | 32 |
| Pseudomonas | Hydrolyses G agents | 33 |
| *Alteromonas undi* | Hydrolyses soman preferentially | 17 |
| Squid | Hydrolyses tabun, VX poorly | 34 |

EXAMPLE 10

Additives to the Sponge to Improve Decontamination of Soman (GD) Contaminated Skin of Guinea Pigs Sponges approximately 1½×2½×¼" (H×L×D) contained 9.0 mL of additive and a second sponge contained 4.5 mL of additive. Each guinea pig was wiped with the first sponge and then the second sponge after soman (GD) exposure. Survival of the guinea pigs was determined after 24 hours, and the protective ratio determined. The protective ratio is the ratio of the $LD_{50}$ of the sponge containing an additive to the $LD_{50}$ of soman in the absence of sponge. Thus, the higher the $LD_{50}$, then the higher the protective ratio and the more effective the sponge combination is for decontamination of guinea pig skin and protecting the animal from the organophosphate. The sponge was compared to the M291 kit, the currently used decontamination kit fielded by the U.S. Army. As shown in the table, the sponges provide 4 to 5-fold better protection than the M291 kit.

FIG. 24A shows the protection afforded by tetraglyme; FIG. 24B the protection afforded by HI-6, and FIG. 24C the protection afforded by 2-PAM. The number on the top of each bar shows the number of guinea pigs evaluated at the indicated dose of soman (GD). For reference, the $LD_{50}$ of soman on guinea pigs without any effort to decontaminate is shown by the label "GP", while the protection offered by the M291 kit is shown by "M291". Other additives to the sponge such as triacetin also afforded some additional protection compared to the M291 kit.

| Additive to sponge | $LD_{50}$ | Protective Ratio |
|---|---|---|
| HI-6 (oxime, 50 mM) | 79 | 8.0 |
| 2-PAM (oxime, 50 mM) | 76 | 7.7 |
| Tetraglyme (30%) | 88 | 8.9 |

| Additive to sponge | $LD_{50}$ | Protective Ratio |
|---|---|---|
| Reference values | | |
| M291 decon kit | 17.7 | 1.8 |
| Soman alone | 9.9 | — |

EXAMPLE 11

Remote Quantitative and Qualitative Analysis of OP Compound

As an OP inhibited enzyme is not readily reversible and the enzyme is immobilized, the material may be transported from the test site to another site to be analyzed for the presence and amount of given OP compounds. Additionally, the material may be left at a site to monitor OP compounds for a period of time. Since the OP inhibited enzyme is not readily reversible, interfering compounds and compositions may be removed from the material either at the test site or at a different location. Furthermore, the analysis need not be conducted immediately or soon after sampling.

A. Fluoride-Induced Release of OP

High concentrations of F− cause the release of OP compound complexed to the inhibited ChE immobilized on the material. See FIG. 14. This results in a soluble phosphofluoridate, which is specific for the OP compound present. The phosphofluoridate may be identified and quantified by gas chromatography and further verified with mass spectrometry in order to determine the original OP compound. Specifically, a material containing the inhibited ChE and washed free of interfering compounds is acidified to pH 4 and incubated with 2M potassium fluoride. The solution is then extracted with a $C_{18}$ SepPak (Waters Associate, Milford, Mass.). The OP compound is eluted and identified by gas chromatography and mass spectrometry. Most of the OP agents of interest may be identified and discriminated from OP pesticides. In this example, the samples need not be frozen in order to be tested for OP compounds at a later date since the material is extremely resistant to mechanical stress, harsh chemical conditions, and extreme and varying temperatures.

B. Enzymatic Digestion

As an alternative procedure, enzymatic digestion may be used for post-exposure identification of OP compounds. The OP compounds may be released from the enzymes immobilized on or within the porous support and digested with 1M Tris buffer, pH 10, and alkaline phosphatase. Then the high molecular weight products may be concentrated, dissolved in a solution of pyridine and trimethylsilylation agents. The samples can then be analyzed by gas chromatography and mass spectrometry.

EXAMPLE 12

Figure 25:
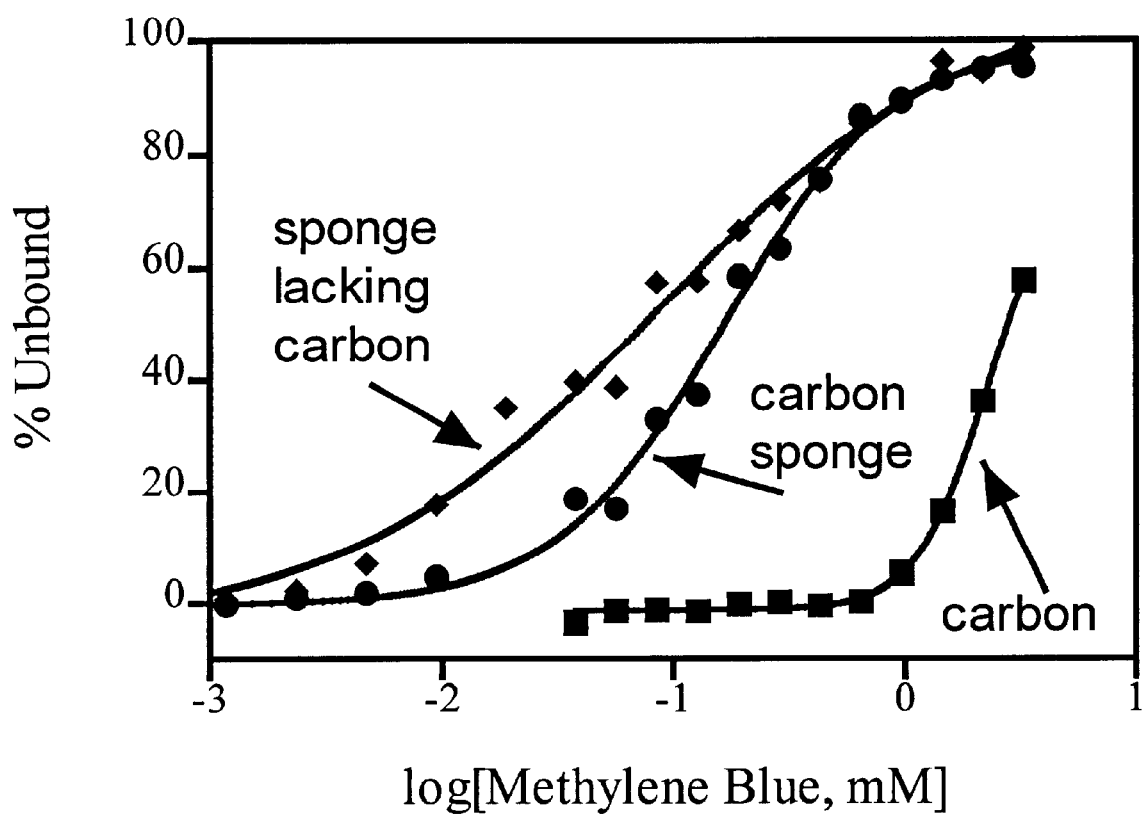
FIG. 25 illustrates the capacity of the resulting carbon sponge for binding methylene blue (a calorimetric indicator for activated carbon).

Activated Carbon Containing Sponge 0.5–1 grams of activated carbon was added to about 1 mL of the prepolymer prior to mixing with acetylcholinesterase (5 mL of Electric eel, in 50 mM pH 8.0 phosphate buffer with 1% Pluronic P-65) to produce an acetylcholinesterase immobilized carbon sponge. The addition of carbon did not interfere with the immobilization of the enzyme, as shown in the table. The capacity of the resulting carbon sponge for binding methylene blue (a calorimetric indicator for activated carbon) is illustrated in FIG. 25. Therefore, comparison of the sponge with activated carbon to the sponge lacking activated carbon demonstrates that it can bind about 2-fold more methylene blue at less than saturating concentrations.

Activities of Sponges and Activated Carbon

| Type of Sponge | Relative Activity (% control in absence of carbon) | Relative Activity to absorb methylene blue |
|---|---|---|
| Electric eel AChE sponge | 100% | 1X |
| Electric eel AChE sponge with Activated Carbon | 108% | 2X |
| Activated Carbon not in the sponge | — | 13X |

EXAMPLE 13

On-Site Qualitative and Quantitative Determination of OP Compounds

Qualitative and quantitative determination of OP compounds may be conducted on-site by utilizing a plurality of indicators encapsulated and embedded on or within the porous support. The indicators may be encapsulated in a structure which is easily broken by mild-pressure, as a liposome or a tiny crushable packets. Thus, one may use the material to decontaminate or detoxify an area then squeeze the material to release the indicator from the tiny crushable packet or liposome. The change in color will indicate the amount of or type of OP compound the material decontaminated or detoxified.

EXAMPLE 14

Multiple Uses of the Differentially Acting Material

A sponge of desired size with immobilized enzymes, e.g. ChEs, choline oxidase and peroxidase, may be synthesized with built-in carbon electrodes. See FIG. 13. The electrodes would be immersed within the enzyme containing, sponge, and would reflect the activity of the enzyme in the surrounding area. The carbon electrode may be plugged into a hand-held and battery operated electrochemical detector. When substrate is added, e.g. acetylthiocholine or acetylcholine, the electrode will yield a response if the sponge is not exhausted and can detoxify additional OPs. In this manner, the sponge will act as a detoxifying sponge and as a biosensor in an alternative mode.

Additionally, the carbon electrodes may be inserted into various areas of a cured foam. In the event of a terrorist attack, and in the presence of substrate, the carbon electrodes could convey information about the OP compound in the environment to a central collection point.

Alternatively, the foam could be sprayed with substrate, which may be calorimetric, chemiluminescent or fluorescent, so that a chance in foam color, i.e. chemiluminescent or fluorescent, would indicate that the foam is active and that there is no leakage of OP compound or pesticide. Lack of color change would indicate such things as a defective indicator, not enough enzyme was administered, the OP compound was not sufficiently contained by the foam, defective enzyme was utilized or the oxime was consumed. Therefore, the location where color is absent would indicate the need to spray additional or different foam. A positive control, i.e. biosensor, may be used to determine whether or not the indicator is defective.

The sponge containing immobilized enzyme could be used to soak up the OP or pesticide and placed in a plastic bag to complete decontamination of the chemical toxin. After a period of time, substrate in crushable vials or packets included in the plastic bag could be released by manual crushing. A strong color development would indicate effective detoxification. Several crushable vials or packets may be included so that the completion of decontamination could be tested several times. For example, if after the first test, an insufficient color change would show that insufficient time had elapsed to complete decontamination. The sufficiency of decontamination could be rechecked at a later time by simply crushing another vial. As several vials were originally included in the bag, reopening the bag is unnecessary and therefore avoids further exposure to the OP compound or insecticide. Further, if the substrate were a chemiluminescent, the decontamination may be evaluated in the dark without a power source.

The material containing multiple enzymes may be synthesized in a shape suitable to allow water to flow through it or around it, such as in a column or a chamber in order to bind all the OPs. A portion of the material could be removed and placed with a crushable packet to release substrate. Color development would indicate detoxified water. The material could be reused. It would not, most likely, have reactivating oxime because then the oxime would leach to the drinking water.

Again, lack of color change would indicate such things as a defective indicator, not enough enzyme was administered, defective enzyme was utilized or the oxime was consumed. Therefore, lack of color change would indicate the need to utilize an additional or a different sponge. A positive control, i.e. biosensor, may be used to determine whether or not the indicator is defective. Additionally, if the indicator is not defective and the sponge did not develop color, it could be reactivated with oxime for other detoxifying purposes.

EXAMPLE 15

Long-term Sensing of Aqueous Environments for Organophosphates

A significant advantage of the immobilized enzymes is that they are covalent immobilized permanently within the polyurethane matrix. This affords the sensors with the following properties that are absent in the soluble state of the enzymes or when the enzymes are non-covalently attached to papers, tickets, or other indicating strips.

A. Ability to Retain Activity After Continuous Incubation at 25° C. at Different pHs The activity of immobilized AChE and BCHE enzymes after 2 months at 25° C. in buffers at pHs from 4.0 to 10.5 are shown in FIGS. 26A and 26B, respectively. Even after more than a month in solution without sterilization, both ChE sensors retained most of their original activity at pHs between 6–8, and significant activity was only lost at the extremes of pH4 and 10.5. The loss of activity at the extreme pHs is not unexpected since it is known that these conditions cause irreversible denaturation of the soluble enzymes. However, note that for short periods of less than a few days, 50% or more of the original activity of the immobilized enzymes remained, while the soluble enzyme would have been completely denatured. These results demonstrate that the ChEs are suitable for long-term (days to many weeks) detection of OPs. For instance, the sensor could be left at a remote location and retrieved at a later date.

B. Ability to Retain Activity After Continuous Incubation in Natural Water Sources at Ambient (25° C.) Temperatures Additional evidence that the AChE sensor retains activity for extended periods in the environment is observed in FIG. 26C (Exposure to Brackish Water, obtained from the Chesapeake Bay, Aberdeen, Md.) and FIG. 26D (Exposure to Fresh Water, obtained from the Allegheny River, Pa.). Most of the original activity of the sensor remains even when exposed to water for over 1 month. The immobilized enzyme was also resistant to natural microbiological flora and fauna that could degrade the enzyme since autoclaved water was not more stable than untreated water. Taken together, these results demonstrate the long-term sensing potential of these immobilized enzymes.

C. Comparison of the M272 Ticket with Example A and B, Above

The M272 ticket (Available from Truetech, Inc.) is the currently fielded ticket for sensing organophosphates in aqueous solutions. The ticket contains non-covalently bound Eel cholinesterase. In contrast to the 1–2 months that the immobilized AChE and BChE sensors can retain activity even after continuous exposure to natural water sources, varying pH, temperature (up to years), etc, the M272 ticket looses more than 80% of its activity after exposure to Chesapeake Bay water (FIG. 26E) or a buffer (50 mM phosphate buffer, pH 8.0 (FIG. 26F) after only 5 minutes of exposure. Therefore, while the immobilized enzymes are suitable for long-term monitoring of the environment including water, in contrast, the M272 ticket is not suitable for even short-term monitoring of water sources for organophosphorus compounds.

EXAMPLE 16

Enzyme Coupling Prior to Formation of the Material

The enzymes may be coupled together prior to formation of the material by means known in the art to form a cross-linked enzyme complex. See e.g Hashida, S., Imagawa, M., Inoue, S., Ruan, K.-h, and Ishikawa, E. (1984) J. Applied Biochem. 6, 56–63 and Samaoszuk, M. K., Petersen, A., Lo-Hsueh, M., and Rietveld, C. (1989). (A peroxide-generating immunoconjugate directed to eosinophil peroxidase is cytotoxic to Hodgkin's disease cells in vitro.), Antibody Immunocon. Radiopharm. 2(1), 37–46.

For example, AChE may be conjugated to choline oxidase with one of the various cross-linkers and methods known in the art. Therefore, AChE and choline oxidase would be in close proximity so the product of AChE hydrolysis, choline, would fall right next to the choline oxidase to produce $H_2O_2$. This type of enzymatic cascade would provide more efficient coupling and a faster and more sensitive response. In addition, because of the proximity of choline oxidase, i.e. choline oxidase to AChE, the ratio of choline oxidase to AChE may be reduced. More than two different enzymes may be utilized.

The cross-linker utilized may be a multifunctional cross-linking agent. A wide variety of cross-linking agents are available from commercial suppliers, i.e. Pierce (Rockford, Ill.). These multifunctional cross-linking agents may comprise varying lengths of spacer arms to ensure that the bridge between the linked enzymes is an appropriate length for maintaining independent enzyme structure, function and activity. Typically, this would be a length of about 4–8 angstroms. However, the length may be up to 16 angstroms. Some cross-linking sites must be available for coupling the conjugated enzymes to the prepolymer. The cross-linking may be performed in the same buffer as used for the prepolymer reaction as explained in Example 2. The enzyme conjugate is then mixed with a prepolymer, as in Example 2, to form a polymeric material.

EXAMPLE 17

Sensitivity of Soluble and Immobilized Mammalian AChE to Pesticide (Dichlorophos) and Organophosphate (Soman, GD)

AChE sensor and soluble AChE were exposed to dilutions of dichlorophos in 2.5 mL of 50 mM phosphate buffer for 5 minutes, and then the activity of the enzymes in soluble form and immobilized sensor were determined. As shown in FIG. 27A, the sensitivity of the immobilized sensor and soluble enzyme exhibited very similar $EC_{50}$ values, however the slope for the sponge was about 20% less than the soluble enzyme. These results indicate that the AChE-sponge was slightly less sensitive to inhibition by the pesticide than the soluble mammalian enzyme.

Similar results were observed for the inhibition of AChE sensor (immobilized enzyme) and the soluble acetylcholinesterase. FIG. 27B demonstrates that when the enzymes are exposed to soman for 5 minutes and then inhibition of the enzyme determined, the curves indicating loss of enzyme activity by soman exposure are not significantly different. Thus, in the absence of soman, there is color development and enzyme activity (100% level) while at 30 pg of soman, little color reaction develops and activity is less than 20% of the control level.

REFERENCES CITED IN TABLE 5

(17) DeFrank, J. J., Beaudry, W. T., Cheng, T-C., Harvey, S. P., Stroup, A. N., and Szafraniec, L. L. Screening of halophilic bacteria and Alteromonas species for organophosphorus hydrolyzing enzyme activity. Chem.-Biol. Interactions 87:141–148 (1993).

(33) Donarski W. J., Dumas D. P., Heitmeyer D. P., Lewis V. E., Raushel, F. M. Structure-activity relationships in the hydrolysis of substrates by the phosphotriesterase from *Pseudomonas diminuta*. Biochemistry 28:4650–5 (1989).

(32) Furlong, C. E., Richter, R. J., Chapline, C. and Crabb, J. W. Purification of rabbit and human serum paraoxonase. Biochemistry, 30:19133–10140 (1991).

(13) Gan, K. N., Smolen, A., Eckerson, H. W., La Du, B. N. Purification of human serum paraoxonase/arylesterase. Evidence for one esterase catalyzing both activities. Drug. Metab. Disp. 19:100–106 (1991).

(34) Hoskin, F. C., Roush, A. H. Hydrolysis of nerve gas by squid-type diisopropyl phosphorofluoridate hydrolyzing enzyme on agarose resin. Science 215:1255–7 (1982).

(2) Maxwell, D. M., C. A. Castro, D. M. De La Hoz, M. K. Gentry, M. B. Gold, R. P. Solana, A. D. Wolfe, B. P. Doctor. Protection of rhesus monkeys against soman and prevention of performance decrement by treatment with acetylcholinesterase, Toxicol. Appl. Pharmacol. 115 44–49 91992).

(21) Personal Communication, Dr. Gabriel Amitai, Israel Institute for Biological Research, Ness Ziona, Israel.

(1) Taylor, P., Anticholinesterase agents, in: A. G. Gilman, T. W. Rall, A. S. Nies, P. Taylor (Eds.), The Pharmacological Basis of Therapeutics, Pergamon, New York, pp. 131–149 (1990).

Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. A reusable polymeric sponge or foam for the detoxification of a diverse array of organophosphorus and/or organosulfur compounds comprising a plurality of enzymes or a cross-linked enzyme complex of said plurality of enzymes immobilized on the sponge or foam, said plurality of enzymes comprising multiple-enzymes selected from the group consisting of acetyicholinesterase (AChE), butyrylcholinesterase (BChE), triesterase, pseudocholinesterase, choline oxidase, peroxidase, organophosphate hydrolase (OPH), phosphotriesterase, paraoxonase, and laccase and an indicator embedded in the sponge of foam for measuring the capacity of the sponge or foam for detoxification of organophosphorus and/or organosulfur compounds, wherein the indicator is fluorescent, chemiluminescent or visible chromogen or is an electrode, and said indicator is encapsulated in a lipsome or is in a crushable packet.

2. The polymeric sponge or foam of claim 1 wherein the sponge or foam comprises polyurethane.

3. The polymeric sponge or foam of claim 1 further comprising carbon embedded or integrated on or in the sponge or foam.

4. The polymeric sponge or foam of claim 1 further comprising a reactivation compound, material or device.

5. The polymeric sponge or foam of claim 4 wherein said reactivation compound, material or device comprises 1-(2-hydroxy iminomethyl-1-pyridium-1-(4-carboxyaminopyrididinium)-dimethyl ether hydrochloride (HI-6), N,N-trimethylene bispyridinium-4-aldoximme dibromide (TMB4), or mono or bisquarternary.

6. The polymeric sponge or foam of claim 1 wherein said polymeric sponge or foam is color-coded.

7. A kit for the detoxification of an array of organophosphorus and/or organosulfur compound comprising the polymeric sponge or foam of claim 1 and a compound or compounds for enzyme reactivation selected from the group consisting of 1-(2-hydroxy iminomethyl-1-pyridium-1-(4-carboxyaminopyrididinium)-dimethyl ether hydrochloride (HI-6), N,N-trimethylene bispyridinium-4-aldoximme dibromide (TMB4) and mono or bisquarternary oximes.

8. The polymeric sponge or foam of claim 1 wherein said plurality of enzymes are organophosphate hydrolase (OPH) and either acetylcholinesterase (AChE) or butyrycholinesterase (BChE).

9. A method of reactivating the polymeric sponge or foam of claim 1 comprising contacting said polymeric sponge or foam with at least one compound selected from the group consisting of: 1-(2-hydroxy iminomethyl-1-pyridum-1-(4-carboxyaminopyrididinium)-dimethyl ether hydrochloride (HI-6), N,N-trimethylene bispyridinium-4-aldoxime dibromide (TMB4) and mono or bisquarternary oximes.

10. A method for decontaminating a surface where one or more organophosphorus and/or organosulfur compounds may be present comprising contacting the surface with the polymeric sponge or foam of claim 1.

11. The method of claim 10 further comprising measuring the capacity of the sponge or foam for detoxification of the organophosphorus and/or organosulfur compounds.

* * * * *